(12) United States Patent
Boas et al.

(10) Patent No.: US 7,047,055 B2
(45) Date of Patent: May 16, 2006

(54) FETAL PULSE OXIMETRY

(75) Inventors: David Alan Boas, Newmarket, NH (US); Anna Zourabian, Waltham, MA (US)

(73) Assignees: The General Hospital Corporation, Boston, MA (US); The University, Boston, MA (US)

( * ) Notice: Subject to any disclaimer, the term of this patent is extended or adjusted under 35 U.S.C. 154(b) by 0 days.

(21) Appl. No.: 10/415,163

(22) PCT Filed: Jan. 26, 2001

(86) PCT No.: PCT/US01/02646

§ 371 (c)(1),
(2), (4) Date: Feb. 5, 2004

(87) PCT Pub. No.: WO01/54573

PCT Pub. Date: Aug. 2, 2001

(65) Prior Publication Data

US 2004/0116789 A1 Jun. 17, 2004

Related U.S. Application Data

(60) Provisional application No. 60/179,063, filed on Jan. 28, 2000.

(51) Int. Cl.
*A61B 5/00* (2006.01)

(52) U.S. Cl. .................................................. 600/338
(58) Field of Classification Search ............. 600/310, 600/322, 323, 330, 336, 338
See application file for complete search history.

(56) References Cited

U.S. PATENT DOCUMENTS

| 4,714,341 A | 12/1987 | Hamaguri et al. |
| 4,938,218 A | 7/1990 | Goodman et al. |
| 4,984,574 A * | 1/1991 | Goldberg et al. ............ 600/410 |
| 5,099,842 A | 3/1992 | Mannheimer et al. |
| 5,109,849 A | 5/1992 | Goodman et al. |
| 5,228,440 A * | 7/1993 | Chung et al. ............... 600/338 |
| 5,247,932 A | 9/1993 | Chung et al. |
| 5,348,002 A * | 9/1994 | Caro .......................... 600/310 |
| 5,411,024 A | 5/1995 | Thomas et al. |
| 5,421,329 A * | 6/1995 | Casciani et al. ............ 600/338 |
| 5,511,553 A | 4/1996 | Segalowitz |
| 5,743,260 A | 4/1998 | Chung et al. |
| 5,776,058 A | 7/1998 | Levinson et al. |
| 5,813,980 A | 9/1998 | Levinson et al. |
| 5,879,293 A | 3/1999 | Hojaiban et al. |
| 5,911,690 A * | 6/1999 | Rall ........................... 600/338 |

FOREIGN PATENT DOCUMENTS

WO    WO 99/40842    *   8/1999

OTHER PUBLICATIONS

Zourabian et al. "Trans–abdominal monitoring of fetal arterial blood oxygenation using pulse oximetry" *Journal of Biomedical Optics* 5(4):391–405 (Oct. 2000).

R. Choe et al., "Feasibility of frequency domain NTR spectrometer to measure fetal cerebral blood oxygenation in–utero," pp. 661–668, Part of the SPIE Conference on Optical Tomography and Spectroscopy of Tissue III, San Jose, CA, Jul. 28, 1999, SPIE vol. 3597.

(Continued)

*Primary Examiner*—Eric F. Winakur
(74) *Attorney, Agent, or Firm*—Fish & Richardson P.C.

(57) ABSTRACT

A fetal blood pulse oximetry method and apparatus using a first wavelength of light at about 655 to 705 nm and a second wavelength of light at about 820 to 900 nm. Measurements are taken through a mother's abdomen. Processing is performed to extract absorption information related to fetal arterial blood with calculation of fetal oxygen saturation from the extracted data.

18 Claims, 13 Drawing Sheets

OTHER PUBLICATIONS

A. Zourabian et al. "Non–invasive trans–abdominal Monitoring of Fetal Cerebral Oxygenation Using Pulse Oximetry," pp. 669–675, Part of the SPIE Conference on Optical Tomography and Spectroscopy of Tissue III, San Jose, CA, Jan. 1999, SPIE vol. 3597.

A. Zourabian et al. "Non–invasive trans–abdominal Monitoring of Fetal Cerebral Oxygenation Using Pulse Oximetry," Abstract, distributed at SPIE conference, 2 pages, Jan. 23, 1998.

A. Zourabian et al. "Fetal Pulse Oximetry", 14 pages, Slide presentation at SPIE conference, Jan. 28, 1998.

European Search Report for the 01906715.6 European Patent application dated Apr. 7, 2005, 4 pages.

"Continuous monitoring of fetal oxygen saturation by pulse oximetry," *Obstet Gynecol* 1995 Feb; 85(2): 183–6.

"Intrapartum fetal pulse oximetry: past, present, and future," *Am J Obstet Gynecol*, 1996 Jul; 175(1): 1–9. Review.

J. Clint Monit, "Reflectance pulse oximetry at the forehead of newborns: the influence of varying pressure on the probe," 1996 Nov.; 12(6):421–8.

J. Clin Monit, "Validation of reflectance pulse oximetry: an evaluation of a new sensor in piglet," 1997 Jan. 13(1):43–9.

"Anteparturn fetal pulse oximetry," Eur J Obstet Gynecol Reprod Biol. 1997 Mar.: 72 Suppl: S81–5.

"Wavelength selection for low–saturation pulse oximetry," LEEE Trans Biomed Eng. 1997 Mar.; 44(3): 148–58.

"Multicenter study on the clinical value of fetal pulse oximetry. II. Compared predictive values of pulse oximetry and fetal blood analysis. The French Study," Group on Fetal Pulse Oximetry. Am. J. Obstet Gynecol. 1997 Sep; 177(3):593–8.

"Intrapartum reflectance pulse oximetry: effects of sensor location and fixation duration on oxygen saturation readings," J. Clin. Monit. 1997 Sep; 13(5):299–302.

"Fetal oxygenation saturation monitoring in labor: an analysis of 118 cases," Aust. N Z J Obstet Gynaecol. 1997 Nov; 37(4);397–401.

"Maternal position and fetal pulse oximetry," Int J. Gynaeccol Obstet. 1998 Jan;60(1):67–68.

"Fetal oxygen saturation and uterine contractions during labor," Am. J. Perinatol. 1998 Jun:15(6):345–9.

"The prediction of fetal acidosis by means of Intrapartum fetal pulse oximetry," Am J. Obstet. Gynecol. 1999 Jan; 180(1 Pt 1):73–81.

"Physio–optical considerations in the design of fetal pule oximetry sensors," Eur J Obstet Gynecol Reprod Biol. 1997 Mar; 72 Suppl:s9–19. Review.

* cited by examiner

CLOSER MODEL TO THE REAL GEOMETRY

REPRESENTATION DURING THE SIMULATIONS

FETAL PULSE OXIMETRY

This application claims the benefit of Provisional Application No. 60/179,063, filed Jan. 28, 2000.

FIELD OF THE INVENTION

The invention is in the field of pulse oximetry.

BACKGROUND OF THE INVENTION

In obstetrics, fetal heart rate monitoring has been the standard for intrapartum assessment of fetal well being. However, oximetry (oxygen saturation monitoring) can markedly improve medical care in many fields, including anesthesiology, intensive care, and newborn intensive care, because oximetry can allow direct assessment of both fetal oxygen status and fetal tissue perfusion. Unfortunately, fetal oxygen saturation monitoring has proven to present several technical obstacles. Pulse oximetry, a subclass of the general field of oximetry, uses changes in arterial blood volume through a heart beat cycle to internally calibrate oxygen saturation measurements.

SUMMARY OF THE INVENTION

The invention is based on the discovery of a pulse oximetry method for non-invasive monitoring of fetal blood oxygenation by directing light in the wavelength range of about 655 to 705 nm (e.g., 665–700, or 700 nm) and light in the range of about 820 to 910 nm (e.g., 830–905, 860–900, or 900 nm) into the abdomen of a pregnant woman, and detecting light scattered and reflected by fetal and maternal tissues back to the surface of the mother's abdomen. The use of these particular wavelengths of light minimizes measurement errors.

Consequently, the invention includes instruments and methods for monitoring fetal oxygen saturation during the 3rd trimester. The oximetry is non-invasive, relying on light passing though the mother's abdomen. The light passing and scattering through the tissue exits the surface of the abdomen with a slight amplitude modulation caused by pulsatile flow in the arteries of both the mother and the fetus. The fetal pulse is distinguishable from the maternal pulse by its frequency difference. Hence, a Fourier transform is performed on the detected signals to separate the generally faster fetal signal from the generally slower maternal signals. The typical fetal heart rate lies between 1.5 and 2.5 Hz, while the maternal heart rate typically lies between 1 and 1.25 Hz.

The methods and devices of the invention can be used to continuously and non-invasively monitor the oxygen saturation of arterial blood in the fetus. The invention is particularly useful in the clinic, where the health of the fetus can be quickly evaluated by examining the oxygen saturation of fetal blood. In addition, combining the measured extent of oxygen saturation with the measured fetal heart rate can arm the health care provider with more information to facilitate diagnosis and recommendations for treatment of the fetus and/or mother, if indicated.

The invention therefore features a method of determining the oxygen saturation of fetal blood by emitting light of a first wavelength (e.g., about 655–705 or 700 nm) onto the abdominal surface of a pregnant mammal over time; emitting light of a second wavelength (e.g., about 820–910 or 830 nm) onto the abdominal surface of the pregnant mammal over time, where the second wavelength is different from the first wavelength; detecting the intensity of light scattered by fetal and maternal arterial blood at the first wavelength and light scattered by fetal and maternal arterial blood at the second wavelength over time, where the time of detection is sufficient to record at least one fetal heart beat and at least one maternal hear beat; converting the detected light into electronic signals; processing the electronic signals (e.g. using a Fourier transform) to separate maternal and fetal contributions to the electronic signals; removing the contributions to the electronic signals generated by maternal arterial blood; measuring the absorption of light at the first and second wavelengths by fetal arterial blood; and calculating the oxygen saturation of the fetal arterial blood from the measured absorption of light over time. The method can further include emitting light of a third wavelength, where the third wavelength is different from each of the first and second wavelengths; detecting the intensity of light scattered by fetal and maternal arterial blood at the third wavelength; and measuring the absorption of light at the third wavelength. Additionally, the method can even further include emitting light of a fourth wavelength, where the fourth wavelength is different from each of the first, second, and third wavelengths; detecting the intensity of light scattered by fetal and maternal arterial blood at the fourth wavelength; and measuring the absorption of light at the fourth wavelength. The method optionally includes removing the contributions to the signals generated by light that never passes through fetal tissue.

In another aspect, the invention features a fetal pulse oximeter including a first light source emitting, light at a first wavelength (e.g., about 655–705 or 700 nm); a second light source emitting light at a second wavelength (e.g., about 820–910 or 830 nm), where the second wavelength is different from the first wavelength; one or more photodetectors suitable for detecting light at the first wavelength and light at the second wavelength, the photodetector capable of distinguishing light at the first wavelength from light at the second wavelength; a probe configured to engage an abdominal surface of a pregnant mammal, the probe coupling the first and second light sources to the photodetector at a substantially fixed position when the probe is engaged to the abdominal surface; and a processor configured to (1) process (e.g., using a Fourier transform) the electronic signals generated by the photodetectors in response to detection of light at the first and second wavelengths, (2) remove the contributions to the signals generated by maternal arterial blood, (3) determine the absorption of light at the first and second wavelengths by fetal arterial blood, and (4) calculate the oxygen saturation of the fetal arterial blood from the absorbed light over time. The oximeter can further include a third light source emitting light of a third wavelength, where the third wavelength is different from each of the first and second wavelengths; and one or more photodetectors suitable for detecting, light at the third wavelength. Additionally, the oximeter can even further include a fourth light source emitting light of a fourth wavelength, where the fourth wavelength is different from each of the first, second, and third wavelengths; and one or more photodetectors suitable for detecting light at the fourth wavelength. The processor is optionally configured to remove the contributions to the signals generated by light that never passes through fetal tissue.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
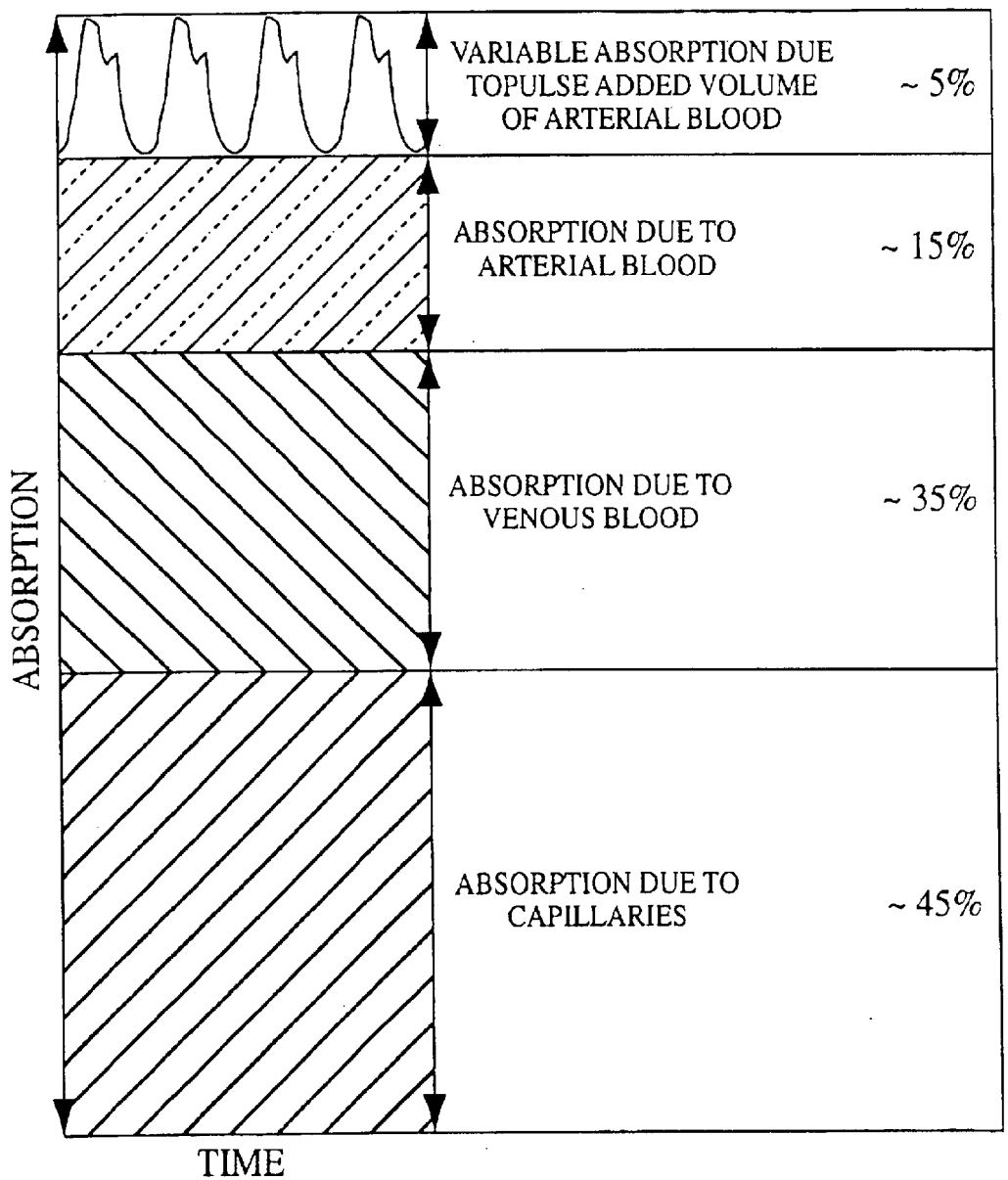
FIG. 1 is a schematic graph showing the relative absorption of various types of blood in the methods of the invention.

The invention relates to pulse oximetry measurements using light of particular wavelengths or range of wavelengths. The light is shone onto the mother's abdominal surface under conditions that allow light to penetrate into the fetus, be absorbed by fetal arterial blood, and scatter back to the surface of the mother's abdomen, where changes in light intensity are measured.

Confirming the adequacy of oxygenation and ventilation is an integral part of monitoring the progress of critically ill patients. Although arterial blood gas analysis (ABGA) has been the gold standard for early detection of arterial hypoxemia and hypercarbia, it is invasive, gives information only intermittently, and frequently imposes a substantial delay between sampling and the availability of results. To obtain a blood sample for ABGA, a needle is placed in an artery, with the radial artery being the usual source of blood used for ABGA. This artery is close enough to the skin surface to be easily entered with a small needle. A blood sample is collected and run through an analyzer. Prior to the development of oximetry, this was the only way to assess a patient's oxygenation.

Pulse oximetry has many of the characteristics of an ideal monitoring technique: portability, noninvasiveness, and the capability for continuous on-line monitoring of arterial oxygen saturation ($SaO_2$). As a means of identifying hypoxia, oximetry serves as another tool to give providers of health care an insight into the patient's condition. In a sense, it acts as an early warning system. An individual's arterial oxygen saturation can fall well below 80% before clinical signs, such as cyanosis or a change in mental status, become evident.

Pulse oximeters of the invention take advantage of the fluctuations in the fraction of arterial blood in the tissue below the sensor. By monitoring the relative fluctuations from measurements at two wavelengths simultaneously, the arterial oxygen saturation is determined by making use of the differences between the absorption spectra of oxy- and deoxy-hemoglobin. Pulse oximetry is standard for monitoring people during anesthesia and in critical-care situations and can be applied for neonatal as well as for adult monitoring.

Electronic fetal heart rate monitoring is almost universally used as the standard for intrapartum assessment of fetal well being and is an indirect measure of fetal oxygenation and acid-base balance. However, the high number of false positives in this method has become a motivation for developing additional means for assessing fetal well being. Such an addition to clinical assessment would, in turn, have the potential to influence clinical management in a manner that would decrease unnecessary fetal and maternal interventions.

Previous research by others has focused on trans-vaginal fetal pulse oximetry in which the sensor was placed on the fetal head or cheek (Dildy et al., Ostet. Gynecol. 81:630–635, 1993). This approach is only feasible during labor and delivery. Also, small complications may occur near the sensor, such as bruises, indentations, or other irritations, that can confound measurements. Furthermore, uterine contractions increase the pressure of the sensor against the fetal scalp, leading to venous pulsations and therefore artifacts in the signal (McNamara et al., Brit. J. Obstet. Gynecol. 102:644–647, 1995). In addition, systematically low readings are obtained during delivery due to increases in scalp congestion, venous pulsations, and the accumulation of extracellular fluid (McNamara, supra; and Dildy et al., Am. J. Ostet. Gynecol. 171:179–184, 1994).

In the following sections, a brief introduction is presented on fetal respiratory and circulatory physiology, as well as oximetry in general and pulse oximetry in particular. As an extension of the theoretical background of pulse oximetry, an optimal wavelength selection analysis is presented, and systematic errors caused by a number of assumptions made during this analysis is discussed. The optical shunt problem (i.e. caused by a fraction of the detected light exiting the medium without reaching the fetus), which can potentially reduce the accuracy of the trans-abdominal measurements, is also demonstrated and evaluated.

Pulse Oximetry

Pulse oximeters are widely used to monitor patient well being (Peterson, Science 232:G135–G140, 1986. Schmitt, IEEE Trans. Biomed. Engineer. 38:1192–1203, 1991; Marble et al., Applied Optics 33:1279–1285, 1994; and Mendelson et al., IEEE Trans. Biomed. Engineer. 35:798–805, 1988), as they provide accurate information on arterial blood oxygen saturation. The advantage of pulse oximetry over oxygen tension monitors is that they provide a rapid response to changes in blood oxygenation and are non-invasive. The first oximeter used in a clinical environment was an ear oximeter, in which the transmission through the ear lobe was measured by a lamp and photocell attached to the ear (Petersen, supra).

This first oximeter did not utilize the pulsation of the arterial blood to extract arterial oxygen saturation, but instead measured average hemoglobin oxygen saturation across vascular compartments. The mechanism is described as follows; the detected transmission of red light was related to changes in oxy-hemoglobin and was compared to the transmission of green light, which is relatively insensitive to changes in oxygen saturation. Subsequently, the red and green wavelength pair used for measuring the optical density of blood was replaced by 660 nm and 805 nm, where 805 was presumed to be at the isosbestic point in the oxy- and deoxy-hemoglobin spectra. The isosbestic point is the wavelength at which the extinction coefficients of oxy- and deoxy-hemoglobin are the same at that wavelength, and therefore the optical density depends only on the total hemoglobin content. Oximetry often requires heating the tissue in order to increase the blood flow, to make it more representative of the arterial blood. In order to calibrate for the effect of multiple scatter, the tissue is squeezed to temporarily remove the blood.

The evolution of the ear oximeter led to development of the pulse oximeter, which avoids the above-mentioned inconveniences. Unlike transcutaneous oximetry, pulse oximetry is not based on an absolute measurement. Instead, it takes advantage of the pulsating nature of arterial blood, and the oxygen saturation values are obtained by taking the log ratio of the transmitted light at the highest and lowest points of a pulse.

The light passing through the tissue exits with a slight amplitude modulation caused by pulsations of the arterial blood. The mathematical model for pulse oximetry is based on an arterial pulse-triggered measurement of the intensity of the light passing through the tissue. Immediately after each heart beat, the arteries temporarily expand, thereby increasing the volume fraction of blood and therefore the absorption of light in the tissue. In other words, the amount of light attenuated by arterial blood varies according to where in each heart beat cycle the measurement is taken.

FIG. 1 is a schematic representation, in the form of a graph, of the relative absorption of different types of blood. The graph shows the static absorption components in tissue, along with one dynamic component; the pulse-added volume of the arterial blood.

The advantage of pulse oximetry over absolute oximetry is that it avoids the need to make the tissue temporarily bloodless for calibration purposes. Instead, it measures the light transmitted through the tissue at the high and low points of the pulse. The difference in the blood content of the tissue between these two points represents the modulation of the arterial blood volume. The logarithmic ratio of the light transmitted at the low point to that transmitted at the peak (at both wavelengths) gives the optical densities necessary for the oxygen saturation calculation.

Fetal Circulation

The fetal respiratory and circulatory systems are substantially different than that of an adult (J. Schmitt, supra). Arterial oxygen saturation in an adult is generally above 95%. In a normal fetus, on the other hand, the arterial oxygen saturation can be as low as 40%. Fetal circulation is briefly reviewed to explain these differences and the implications for the methods and devices of the invention.

The fetus gets its necessary nutrients via umbilical circulation in order to: (a) build new tissues and increase its storage of substrates, and (b) fuel energy metabolism. The transport of oxygen from the atmosphere to fetal tissues travels the following path; Oxygen is first transported into the maternal alveoli by respiration and then diffuses from the alveolar air into maternal blood. Maternal arterial blood pumped by the mother's heart transports oxygen from the lungs to the placenta. In the placenta, oxygen molecules diffuse from maternal to fetal blood. The highly oxygenated blood returning from the placenta to the fetus perfuses fetal organs. Finally, oxygen diffuses from the fetal blood to the cells of the fetal tissues.

Figure 2:
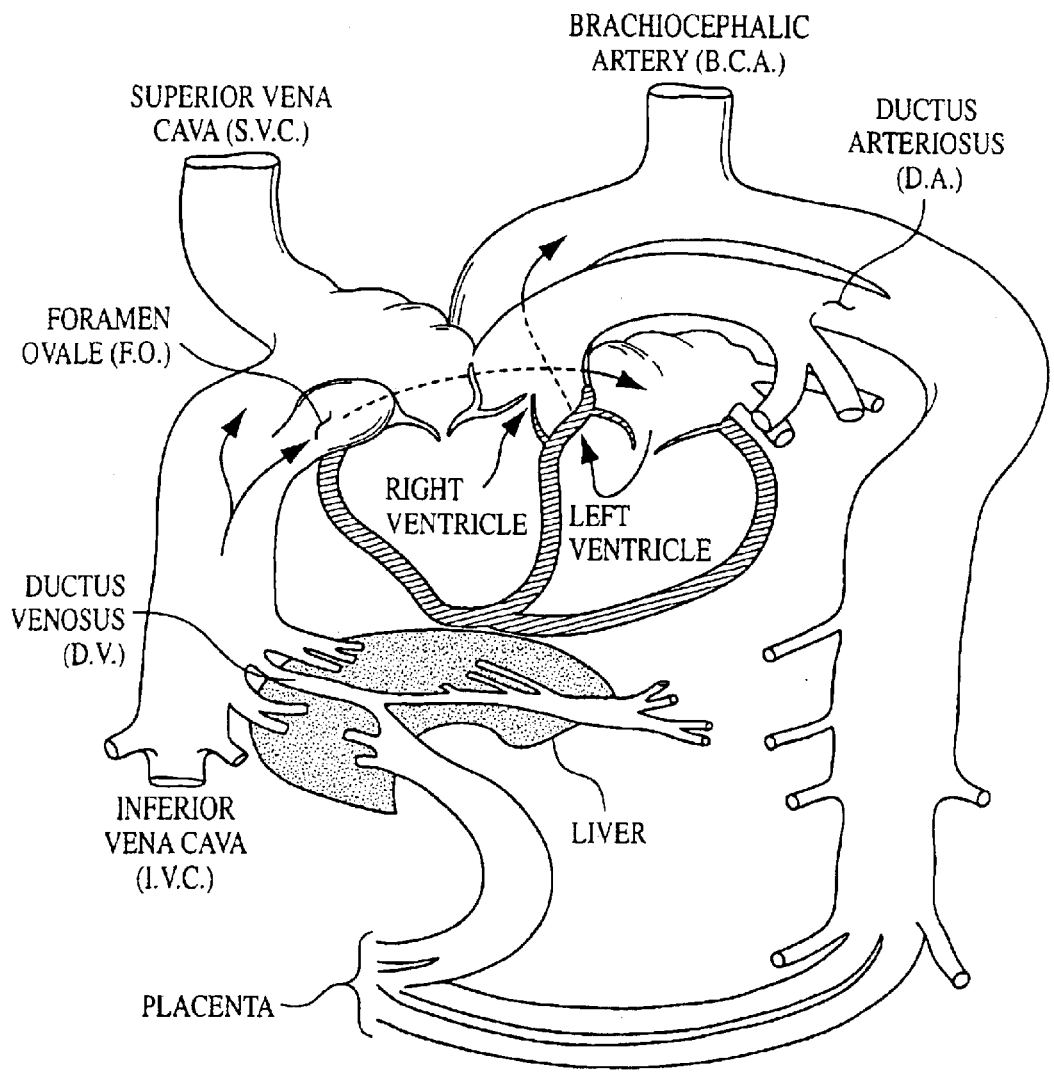
FIG. 2 is a schematic diagram of fetal blood circulation.

The transport of $CO_2$ from fetal tissues to the atmosphere follows the above path but in reverse. Blood carrying oxygen and nutrients flows from the placenta to the fetus via the umbilical vein. Some of that highly oxygenated umbilical venous blood bypasses the liver and enters directly into the inferior vena cava (IVC) via the ductus venosus (see FIG. 2). The remaining blood perfuses the liver. The blood from the IVC, now less oxygenated due to mixing of the placental and IVC blood, enters the right ventricle and is also shunted through the foramen ovale to the left ventricle. Most of the output from the right ventricle bypasses the lungs and flows through the ductus arteriosus into the aorta. When entering the aorta, blood from the ductus arteriosus mixes with blood flowing from ascending to descending aorta, which then perfuses the lower body of the fetus and the placenta. The heart and the upper body are perfused exclusively by blood ejected from the left ventricle.

Umbilical cord gases indicate that fetal arterial oxygen saturation ranges from about 40–70%. These low values are a result of only a fraction of the blood being oxygenated in the placenta with each complete circulation through the body. In adults, about 100% of the blood is oxygenated with each circulation. It is therefore necessary to compensate for this oxygenation difference in any fetal pulse oximeter to ensure that the measurements are accurate at low saturation levels.

In addition, one of the major difficulties during the measurements according to the new methods is the fact that the fetal heart rate can be arrhythmic, making it difficult to resolve the fetal heart rate signal from data collected over more than 30 seconds. Thus, it may be necessary to perform a Fourier transform on segments of time-series data with less than 30 seconds duration to minimize the calculation error introduced by fetal arrhythmia.

Absorption and Scattering

Pulse oximetry measures the absorption of light by chromophores in the tissue by detecting changes in light transmission through, or back reflection from, a vascular bed. The changes in absorption are caused by arterial blood volume increases with each ventricular contraction.

The unique absorption spectrum of an atom or molecule provides a signature for identifying specific compounds. Measuring the concentration of an absorbing species in a sample is accomplished by applying the Beer-Lambert Law. According to that law, the absorption of a sample at a given wavelength is directly proportional to the concentration of the absorbing material, its extinction coefficient, and the pathlength of light through the material. The Beer-Lambert law assumes that the medium is homogeneous, the incident light is collimated, and reflection and scattering do not contribute to the loss of the transmitted light. The Beer-Lambert law is given by:

$$\ln(I_0/I) = \sigma \rho d = \mu_a d \text{ or } \log_{10}(I_0/I) = \varepsilon C d = \frac{\mu_a d}{2.3} = OD = \text{absorbance} \quad (1)$$

where $I_0$ is the incident intensity, $l$ is the transmitted light intensity, $\sigma$ is the absorption cross-section, $\rho$ is the number density of the absorbing molecules, C is the concentration of the absorbing molecules (mM), d is the pathlength (cm), $\varepsilon$ is the extinction coefficient for a solution of molar concentration (molar$^{-1}$ cm$^{-1}$), and $\mu_a$ is the absorption coefficient (cm$^{-1}$).

The Beer-Lambert law does not accurately describe the propagation of light through tissue and has a number of limitations. Of most importance, the law, as written in equation (1), is in general valid only for measurements in non-scattering media and for monochromatic light sources. In addition, equation (1) does not hold true for substances exhibiting dichroism, i.e., substances that have different absorption spectra at different polarizations of light.

The Beer-Lambert relation holds true when specular reflection or scattering do not contribute to the loss of transmitted light. This is clearly not the case in tissue. When the scattering length is shorter than or comparable to the absorption length, then the optical properties cannot be accurately determined using the Beer-Lambert law. The first attempts at diagnostic imaging using optical radiation revealed that multiple scattering, which occurs when visible to near-infrared light propagates through tissue, causes features below the surface to be blurred. As a consequence, measurement of the transmitted intensity through more than a few millimeters of tissue is dominated by scattered light. The characteristic scatter of tissues is commonly expressed in terms of the transport (or reduced) scattering coefficient (corresponding to isotropic scattering):

$$\mu_s' = \mu_s(1-g) \quad (2)$$

where $\mu_s$ is the scattering coefficient and g is the anisotropy factor of scattering equal to the average cosine of the single scattering phase function. For additional discussion, see Arridge. Inverse Problems 15:R41–R93, 1999.

In order to correct for the multiple scattering effect in the tissue we use the Modified Beer-Lambert law:

$$OD = -\log_{10}\frac{I}{I_0} = \sum_i \varepsilon_i C_i L B + G \quad (3)$$

where B is a pathlength factor that accounts for increases in the photon pathlength caused by tissue scattering, and G is the measurement geometry factor, with index "i" represents the $i^{th}$ chromophore. With each ventricular contraction, the arteries expand, increasing the volume fraction of blood and, thereby increasing the absorption of light in the tissue. A change in the chromophore concentration causes the detected intensity to change. $\varepsilon$ and L remain constant, and B and G are assumed to be constant. The change in optical density is then given by:

$$\Delta OD = -\log_{10}\frac{I_{final}}{I_{initial}} = \sum_i \varepsilon_i \Delta C_i L B \quad (4)$$

By considering the contribution of only 2 chromophores, deoxy-hemoglobin (Hb) and oxy-hemoglobin (HbO), the above equation becomes:

$$\Delta OD^\lambda = (\varepsilon_{HbO}{}^\lambda \Delta[HbO] + \varepsilon_{Hb}{}^\lambda \Delta[Hb]) \cdot L \cdot B^\lambda \quad (5)$$

This equation accounts for independent concentration changes in oxy- and deoxy-hemoglobin. The quantity of oxygen in the blood is often expressed as the hemoglobin oxygen saturation (S), which is defined as:

$$S = \frac{[HbO]}{[HbO]+[Hb]} \times 100 = \frac{[HbO]}{[HbT]} \times 100 \ (\%) \quad (6)$$

This expresses tile percentage of the total oxygenated hemoglobin.

By taking the ratio (R) of the changes in optical density measured at two different wavelengths, the following expression is obtained:

$$R = \frac{\Delta OD^{\lambda_1}}{\Delta OD^{\lambda_2}} = \frac{(\varepsilon_{HbO}^{\lambda_1} \cdot S + \varepsilon_{Hb}^{\lambda_1} \cdot (1-S)) \cdot \Delta[HbT] \cdot L \cdot B^{\lambda_1}}{(\varepsilon_{HbO}^{\lambda_2} \cdot S + \varepsilon_{Hb}^{\lambda_2} \cdot (1-S)) \cdot \Delta[HbT] \cdot L \cdot B^{\lambda_2}} \quad (7)$$

By solving for hemoglobin oxygen saturation (S), we obtain the following final expression:

$$S = \frac{\varepsilon_{Hb}^{\lambda_2} \cdot R \cdot (B^{\lambda_2}/B^{\lambda_1}) - \varepsilon_{Hb}^{\lambda_1}}{(\varepsilon_{HbO}^{\lambda_1} - \varepsilon_{Hb}^{\lambda_1}) - R \cdot (B^{\lambda_2}/B^{\lambda_1}) \cdot (\varepsilon_{HbO}^{\lambda_2} - \varepsilon_{Hb}^{\lambda_2})} \quad (8)$$

The B factor can be estimated by solving the photon diffusion equation for the appropriate measurement geometry. For a semi-infinite homogeneous medium, one finds that:

$$B = \frac{1}{2}\left(\frac{3\mu_s'}{\mu_a^{initial}}\right)^{1/2}\left[1 - \frac{1}{1 + L(3\mu_s'^{(initial)}\mu_a^{initial})^{1/2}}\right] \quad (9)$$

This shows that the pathlength factor depends on the absorption, and therefore on the extinction coefficient and wavelength. In practical clinical measurements, this dependence is ignored, and the B parameter is determined empirically. Eq. (9) also shows that the pathlength factor depends on the optode separation and on the tissue scattering.

In summary, eq. (8) shows that if we measure the changes in optical density (caused by arterial pulsations) at two different wavelengths, and if the molar extinction coefficients of the oxy- and deoxy-hemoglobin are known, then the arterial oxygen saturation can be readily calculated.

Wavelength Selection

One of the first oximeters, built in 1935 (Kramer, Klin. Wochenschr. 13:379, 1943), utilized only one wavelength located in the red reunion of the spectrum. Using only one wavelength prevented the device from compensating for changes in hemoglobin concentration. Subsequently, an oximeter using one red wavelength of around 660 nm (for oxy-hemoglobin), and one infrared wavelength as a reference (about 805 nm) was developed. The latter light beam is a wavelength at which the extinction coefficients of both oxy- and deoxy-hemoglobin are the same (isosbestic point), and therefore the optical density depends on the total hemoglobin concentration and not the oxygen saturation. The use of two wavelengths therefore reduces the expression for oxygen saturation to $SaO_2 = a + b(OD^{\lambda_1}/OD^{\lambda_2})$, where the constants a and b are empirically determined.

Given the wavelength dependence of the measurements, a question arises; which wavelengths provide the best saturation sensitivity? In other words, which pair of wavelengths should be chosen to provide the minimum error in calculations and maximum sensitivity to changes in oxygen saturation across a broad range of saturations.

Figure 3:
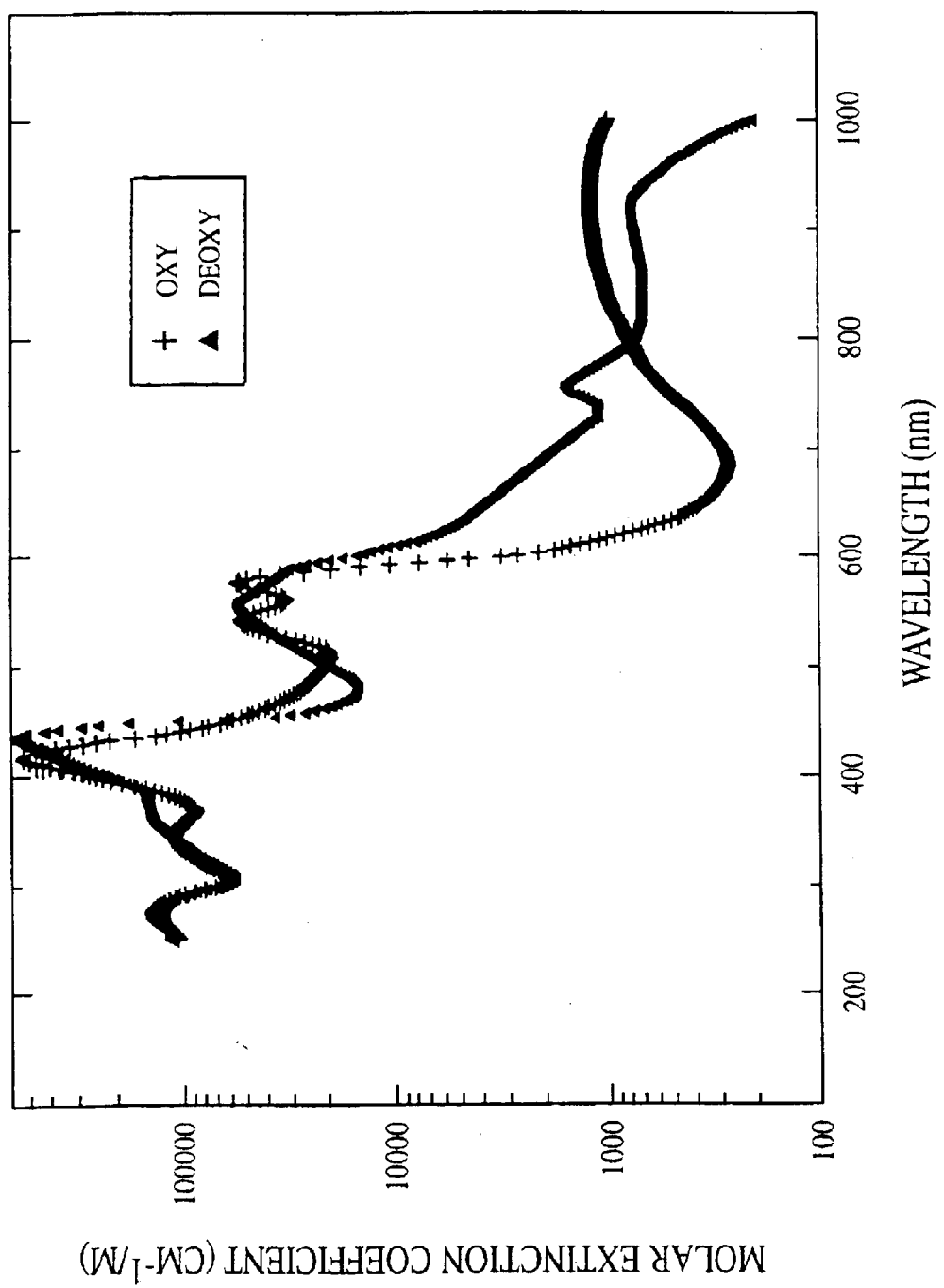
FIG. 3 is a graph of wavelength versus molar extinction coefficient for oxy- and deoxy-hemoglobin. The absorption coefficient is in units of $cm^{-1}$ and is given by $\mu_a=2.3(\epsilon_{HbO}[HbO]+\epsilon_{Hb}[Hb])$, where [HbO] and [Hb] are in molar units.

As we can see from eq. (7) and eq. (8), the saturation depends on the molar extinction coefficients, which in turn are wavelength dependent. The dependence of the molar extinction coefficients of the oxy- and deoxy-hemoglobin is shown in FIG. 3.

The error in oxygen saturation $\sigma_S$ is calculated as:

$$\sigma_S = \frac{\partial S}{\partial R}\sigma_R = \frac{(\varepsilon_{Hb}^{\lambda_2} \cdot \varepsilon_{HbO}^{\lambda_1} - \varepsilon_{HbO}^{\lambda_2} \cdot \varepsilon_{Hb}^{\lambda_1})(B^{\lambda_2}/B^{\lambda_1})}{\left[\varepsilon_{HbO}^{\lambda_1} - \varepsilon_{Hb}^{\lambda_1} - R \cdot (B^{\lambda_2}/B^{\lambda_1})(\varepsilon_{HbO}^{\lambda_2} - \varepsilon_{Hb}^{\lambda_2})\right]^2}\sigma_R \quad (10)$$

where $\sigma_R$, the error in R, is the ratio of the optical densities at two different wavelengths, which is given by:

$$\frac{\sigma_R}{R} = \left[\left(\frac{\sigma_{\Delta OD^{\lambda_1}}}{\Delta OD^{\lambda_1}}\right)^2 + \left(\frac{\sigma_{\Delta OD^{\lambda_2}}}{\Delta OD^{\lambda_2}}\right)^2\right]^{1/2} \quad (11)$$

where $\sigma_{\Delta OD^{\lambda_1}}$ and $\sigma_{\Delta OD^{\lambda_2}}$ are the errors in the optical densities at two different wavelenths. The change in optical density is given by:

$$\Delta OD = (\varepsilon_{HbO}\Delta[HbO] + \varepsilon_{Hb}\Delta[Hb])LB \quad (12)$$

By combining eq. (9) and eq. (12), we obtain for a measurement made on the surface of a semi-infinite medium:

$$\Delta OD = \frac{1}{2}\sqrt{\frac{3\mu_s'}{\mu_a}}\left[1 - \frac{1}{1 + L\sqrt{3\mu_s'\mu_a}}\right](\varepsilon_{HbO}\Delta[HbO] + \varepsilon_{Hb}\Delta[Hb])L \quad (13)$$

where $$\mu_a = 2.3(\varepsilon_{HbO}[HbO] + \varepsilon_{Hb}[Hb]) \quad (14)$$

Figure 4A:
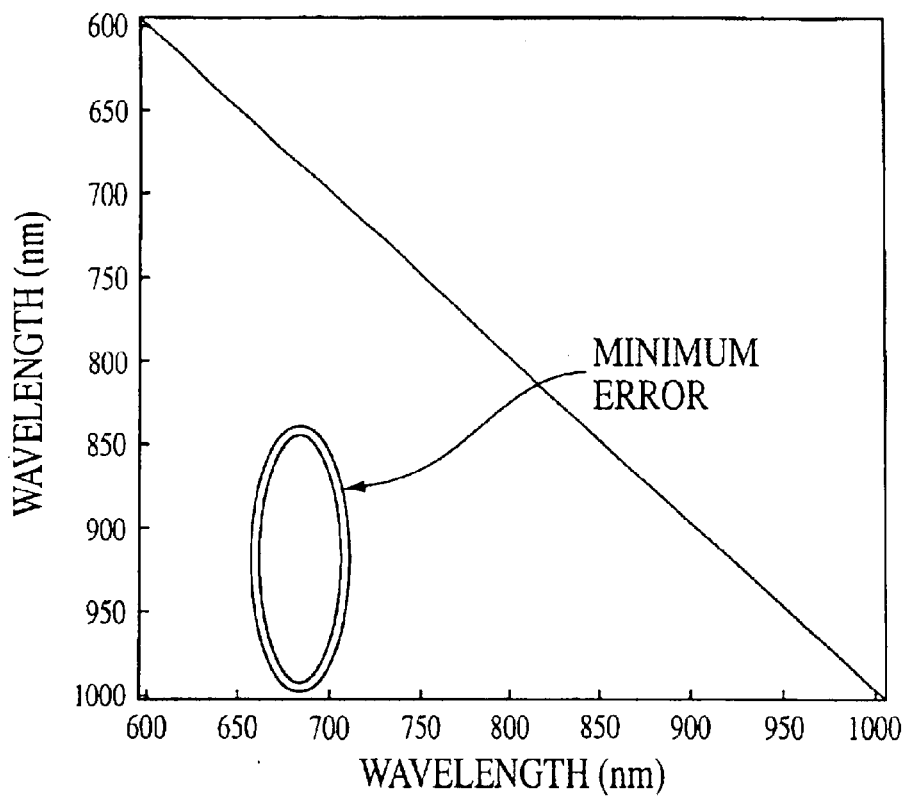
FIG. 4A is a image of the wavelength-dependent saturation error. The scale is $log_{10}$ such that the minimum error is $\sim 10^{-3.5}$. The error for wavelengths of 600 and 650 nm is only slight larger than the optimal wavelength pair of 670 and 925 nm.

By plotting eq. (10) versus wavelength we are able to visualize the wavelength dependence of the saturation error. The resulting dependence is illustrated in FIG. 4A. The image in FIG. 4A is symmetrical around the diagonal axis and was calculated using the following baseline conditions: $\mu_s'=10$ cm$^{-1}$, $[HbO]_{initial}=0.85$ μM, $[Hb]_{initial}=0.15$ μM, a 10% modulation (pulse added volume of oxy- and deoxy-hemoglobin), and L=1 cm. A constant 1% measurement error at both wavelengths, i.e., independent of wavelength, was assumed.

FIG. 4A demonstrates the dependence of the saturation error on wavelengths over the range of 600 to 1000 nm. The image is displayed on a log$_{10}$ scale.

According to the plot, in order to obtain the minimum saturation error, one of the two wavelengths needs to be in the range of 640–720 nm, and the second wavelength in 850 to 1000 nm range. Decreasing the oxygen saturation from 85% to 45% does not change the optimal wavelengths, nor does it have a significant effect on the saturation error.

In this approach, it was assumed that the measurement error remained constant and was independent of wavelength. This assumption is not generally true. The detected signal and its measurement error can change significantly with wavelength due to absorption in the tissue. The wavelength dependence of the measurement error is derived, and the result is implemented in the saturation error calculation.

Assumptions made in the process of the calculation and analysis of the saturation error are:

(A) Hb and HbO are the only absorbing chromophores present in tissue.

(B) Scattering is independent of wavelength.

(C) A constant 1% error in the measurement was assumed ($\sigma_{\Delta OD}$).

There are a number of other chromophores present in the tissue; cytochromes, lipids, met-hemoglobin, carboxy-hemoglobin (HbCO), etc. Lipids do not significantly add to the overall extinction coefficient of the tissue, as it is only present at roughly one-tenth proportion compared to water. Typical concentrations of HbCO are less than 10% of the total hemoglobin content. In addition, the near infrared effect of HbCO is negligible because of its low extinction coefficients in that region of the spectrum. Neglecting the effect of met-hemoglobin, on the other hand, could potentially introduce larger errors in the measurements. However, its tissue concentration is low with respect to the total hemoglobin concentrations. Ignoring the contribution of the met-hemoglobin may introduce error, which can reach 1% of the total hemoglobin signal.

Regarding the second assumption, it is well known that light absorption of compounds present in human tissue greatly depends on the wavelength of the incoming radiation. The scattering dependence on the wavelength, on the other hand, is neglected in most of the cases. In human dermis, scattering dominates over absorption. The forward directed scattering is believed to be due to collagen fibers. Experimental observations reveal that the reduced scattering coefficient decreases with increasing wavelength as $\mu_s' \sim \lambda^{-1.5}$. This dependence is incorporated into our calculation of the wavelength dependent error in $\Delta OD$.

The $\Delta OD$ is calculated from the measured intensities: $\Delta OD = -\log_{10}(\Phi_{final}/\Phi_{initial})$. The fluence is directly proportional to the intensity. Therefore tile absolute error in the change of the optical density is:

$$\sigma_{\Delta OD} = \frac{\partial \Delta OD}{\partial \Phi}\sigma_\Phi \quad (15)$$

The absolute photometric error is $\sigma_\Phi$, which was initially assumed to be constant versus wavelength and saturation. $\sigma_\Phi$ arises from the root-sum-square combination of shot noise and electronic noise as follows:

$$\sigma_\Phi = (\sigma_{electronic}^2 + \sigma_{shot}^2)^{1/2} \quad (16)$$

Electronic noise is introduced when the signals are generated, amplified, and typically fed through an analog-to-digital converter. This noise is assumed to be independent of exposure time, independent of wavelength, and depends only on the electronics of the circuit and is thus assumed constant throughout the experiment.

This occurs at low flux levels, when the signal to noise ratio (S/N) is limited by the shot noise produced by the optical power itself. Since the noise is a function of the square root of the incoming signal power (P(t)), the S/N only increases as the square root of the signal power. A signal carried by N photons will have $\sigma_{shot} = \sqrt{N}$ photons of shot noise. A certain fraction of the detected photons, determined by its quantum efficiency, is detected, and the electrons produced by these photons are then read out. The photon rate (photons per second) can be calculated using the following expression:

$$r = P(t)/h\nu = \lambda P(t)/1.24 \quad (17)$$

where $h\nu(eV) = h\nu/q = hc/q\lambda = 1.24/\lambda(\mu m)$. The signal traveling through the tissue carried by $\Phi$, the photon fluence, will have $\sigma_{shot} = \sqrt{\Phi}$ shot noise. Using the solution to the diffusion equation for semi-infinite media (Haskell et al., J. Opt. Soc. Am 11:2727–2741, 1994), the following was obtained:

$$\Phi = \frac{c \cdot S}{4\pi D}\left[\frac{\exp\left(-\sqrt{3\mu'_s\mu_a} \cdot r_1\right)}{r_1} - \frac{\exp\left(-\sqrt{3\mu'_s\mu_a} \cdot r_2\right)}{r_2}\right] \quad (18)$$

where c is the speed of light in the medium, D is the photon diffusion coefficient given as $D=c/3\mu'_s$; S is the source term with units of power; $r_1$ and $r_2$ are given as follows:

$$r_1 = \sqrt{L^2 + (z_0 - z_S)^2}, \; r_2 = \sqrt{L^2 + (z_0 + 2z_b + z_S)^2};$$

where $z_S$ is the position where the collimated light source (perpendicular to the surface) becomes diffuse inside the medium; $z_i$ is the position of the image source used to satisfy the semi-infinite boundary condition; $z_b$ is the position of the extrapolated boundary; and L is the displacement between the collimated light source and the detector.

The source term in the eq. (18) can be written as $\lambda P(t)/1.24$ (see eq. (17)). An explicit equation for the wavelength dependence of the shot noise is:

$$\sigma_{shot} = \left\{\frac{c\lambda P}{4.96\pi D}\left[\frac{\exp\left(-\sqrt{3\mu'_s\mu_a} \cdot r_1\right)}{r_1} - \frac{\exp\left(-\sqrt{3\mu'_s\mu_a} \cdot r_2\right)}{r_2}\right]\right\}^{1/2} \quad (19)$$

By combining the electronic noise and shot noise terms an expression for the absolute error in our measurement is obtained (see eq. (16)). The main goal of this analysis is to determine how measurement error depends on wavelength. As the electronic noise power is independent of the wavelength, it was assumed constant for the purpose of the analysis. Assuming that $\sigma_{electronic} \ll \sigma_{shot}$, the following expression for the measurement error was obtained:

$$\sigma_{\Delta OD} = \frac{1}{\left\{\frac{v\lambda P}{4.96\pi D}\left[\frac{\exp\left(-\sqrt{3\mu'_s\mu_a} \cdot r_1\right)}{r_1} - \frac{\exp\left(-\sqrt{3\mu'_s\mu_a} \cdot r_2\right)}{r_2}\right]\right\}^{1/2}} \quad (20)$$

Figure 5:
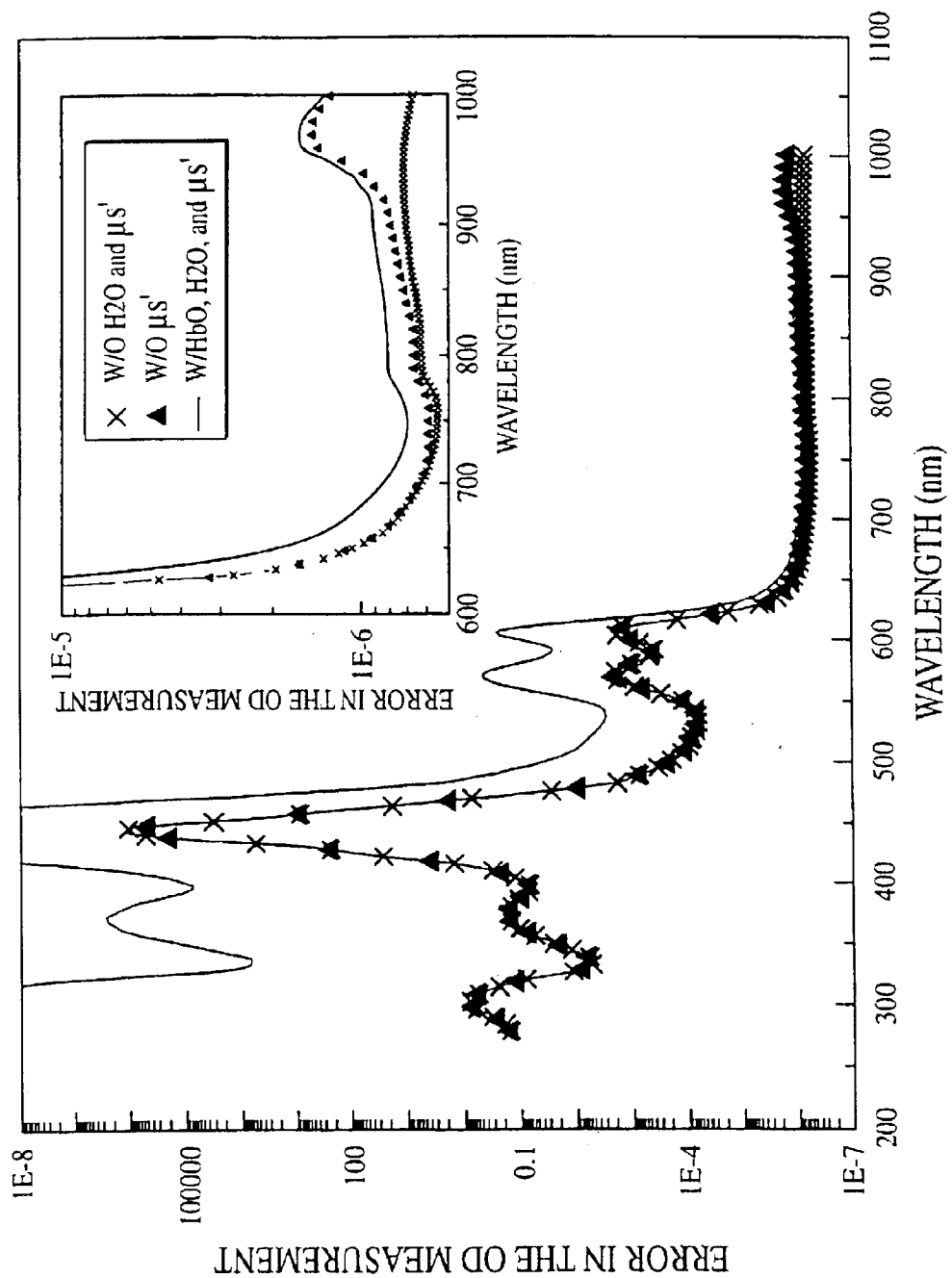
FIG. 5 is a pair of graphs of wavelength versus error in OD measurement, one being embedded in the other.
Figure 6:
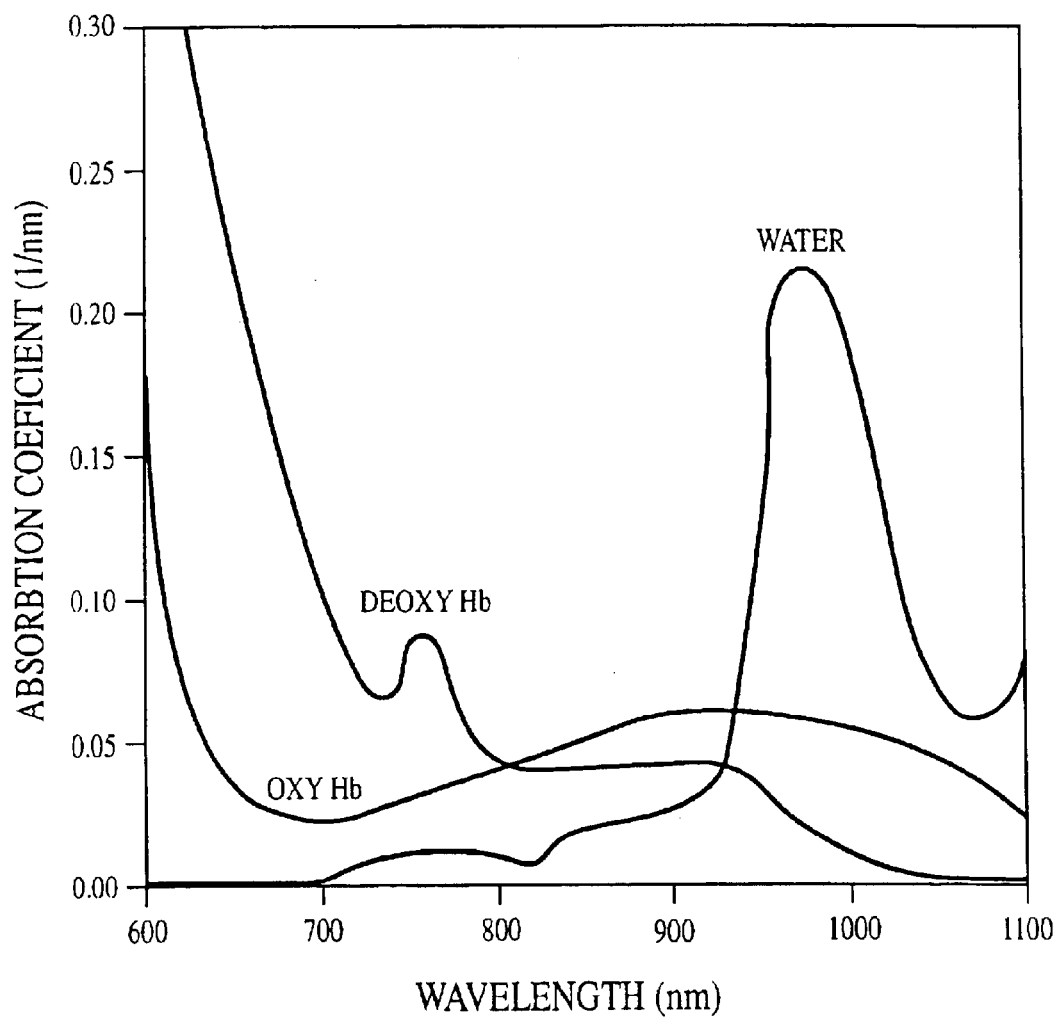
FIG. 6 is a graph of wavelength versus absorption coefficient.

The plot showing the dependence of the measurement error (as $\sigma_{\Delta OD}$) on the wavelength, i.e., the expression given by eq. (20), is shown in FIG. 5. The three curves correspond to 1) error in the measurement without taking into account the water absorption and scattering effects, 2) taking into account the water absorption but not the scattering effect, 3) taking into account both water absorption (along with hemoglobin absorption), and the scattering effect. The average water content in the human body is approximately 65%, therefore the absorption properties of water affect our measurements. The first and second curves (with and without water absorption) look almost identical because at wavelengths below 850 nm, absorption by water is orders of magnitude lower than tile absorption by hemoglobin, and therefore its contribution is insignificant. The absorption of water increases at wavelengths above 900 nm, and consequently the optical signal decreases. The visible and near infrared spectrum of water is presented in FIG. 6, along with the spectra oxy- and deoxy-hemoglobin. The curves show the expected result that stronger scattering at shorter wavelengths has a more pronounced effect on the measurement error.

FIG. 5 demonstrates that the measurement error does indeed depend on the wavelength. This is not surprising, as it is known that the measured signal depends on absorption and scattering by the components in the tissue. In the regions with higher absorption we get higher sensitivity, but with low S/N levels. A stronger signal can be achieved in the 650–900 nm range, where the absorption is still strong enough to provide sensitivity at higher S/N levels.

Figure 4B:
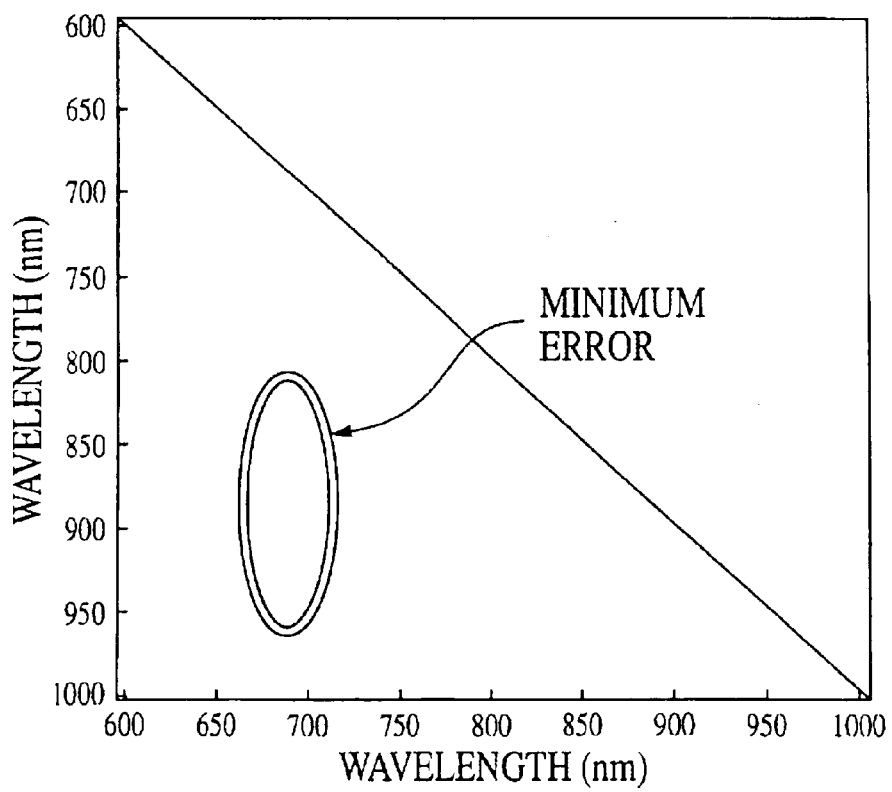
FIG. 4B is a graph of saturation error versus wavelength, taking into account the wavelength dependence of the measurement error on hemoglobin absorption, water absorption, and scattering. The scale is $log_{10}$ such that the minimum error is $\sim 10^{-3.5}$.

The measurement error in the previous wavelength selection simulations are assumed constant at 1% and independent of wavelength. Now, by implementing the wavelength dependence of the measurement, the wavelength dependence of the scattering, and the effect of the water absorption into the saturation error analysis, the results illustrated in FIG. 4B is obtained. This dependence was calculated for 5% whole blood contained in soft tissue, 85% oxygenated hemoglobin, 15% deoxy-hemoglobin, and 10% change in total hemoglobin concentration caused by arterial pulsations. Decreasing the oxygen saturation from 85% to 45% does not change the optimal wavelengths, but does increase the saturation error by approximately a factor of 10.

The simulations and analysis described herein, the goal of which was to choose a pair of wavelengths allowing minimum error in oxygen saturation calculations along with maximum signal strength, leads to choosing the following wavelengths for pulse oximetry: 655–705 nm (e.g., 670–700 nm) and 820–910 nm (e.g., 850–890 nm). This is opposed to 635 nm and 905 nm as determined when neglecting the wavelength dependent measurement error.

The invention will be further described in the following examples, which do not limit the scope of the invention defined in the claims.

EXAMPLES

Example 1

The Optical Shunt Problem

Figure 7:
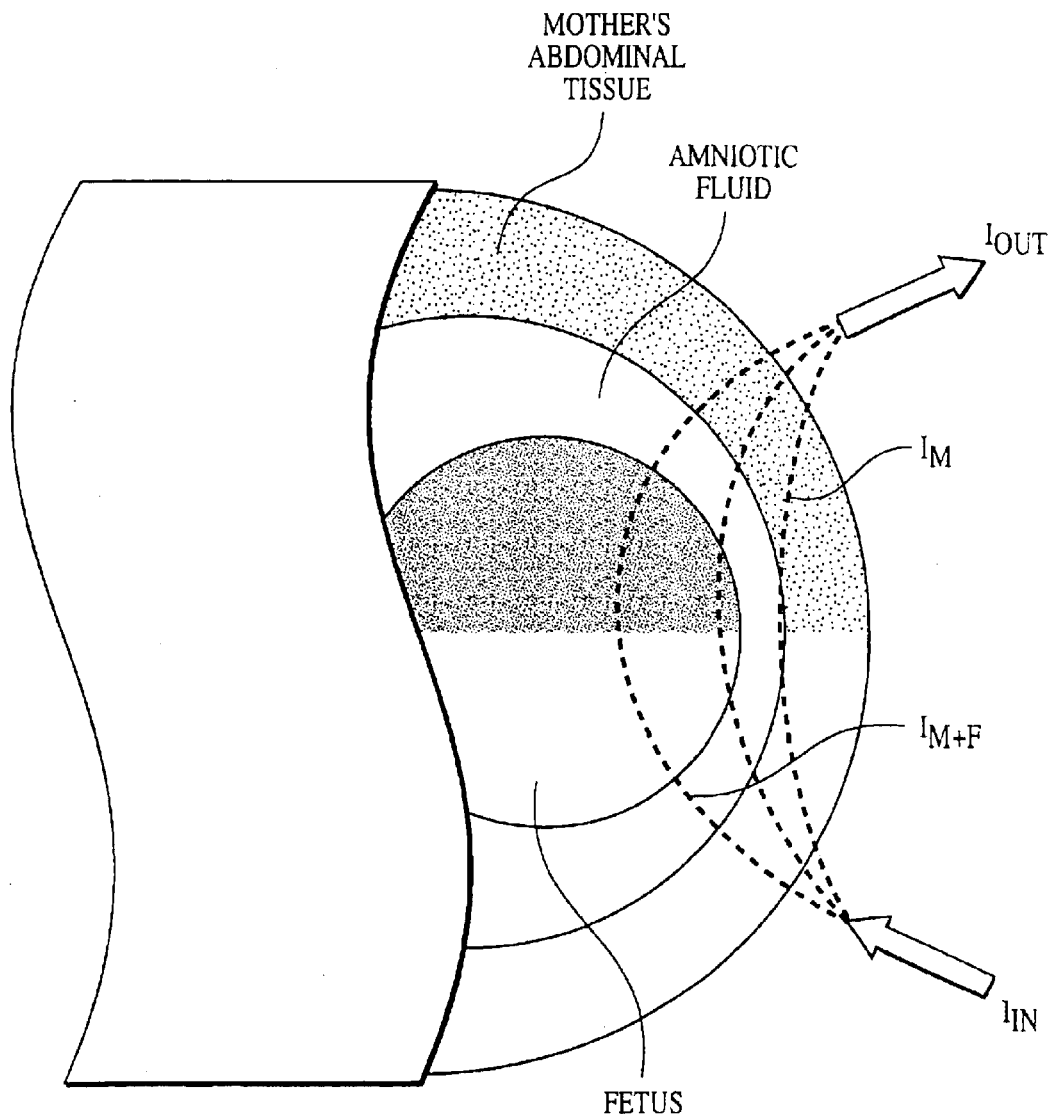
FIG. 7 is a schematic diagram of the optical shunt problem.

A significant percentage of the light emitted into the abdomen of a pregnant individual and back-scattered to the abdominal surface never passes through fetal tissues (FIG. 7). Consequently, a substantial portion of the light detected at the abdominal surface does not provide any information on fetal tissues. This background of maternal signals in which fetal information is embedded is known as the optical shunt problem. To provide a solution to the problem, computer simulations were performed. First, a discussion of the problem is provided.

For fetal pulse oximetry, the approach is to monitor fetal arterial blood oxygenation through the mother's abdomen. This means that the optical radiation from the sources must travel through the mother's tissue, pass through the amniotic fluid separating the fetus from the mother, reach the fetus, and then travel back to a detector located on the mother's abdomen. The detected signal contains information about; 1) mother only—when the source-detector separation is small, and the "banana pattern" (FIG. 7) covers only the maternal tissue; and 2) mother and the fetus—when the source-detector separation is large enough for sufficient light penetration to "see" the fetus. The maternal and fetal contributions to the modulation of the incoming light caused by the pulsations of the arterial blood of the two can be easily separated, as they appear as separate peaks in the Fourier transform. But, the calculation of the oxygen saturation of the modulated signal requires normalization to the DC level of the detected signal, which in our case combines the DC levels from both mother and fetus. As the task of separating the DC levels of two signals (maternal and fetal) is extremely difficult, if not impossible, one must either assume a value for the maternal contribution to the DC level or neglect it. This example investigates the effect that this assumption has on the measurements.

FIG. 7 illustrates the problem described above. The dark outer circle represents a cross-section of the maternal abdomen, the lighter one represents that of the amniotic fluid, and the smallest dark circle represents the fetal body. As shown in the diagram, the incident light samples different parts of the medium, and the exiting intensity is the combination of that light which has traveled through the fetal plus maternal tissue and amniotic fluid ($I_{F+M}$), as well as that light which has traveled only through the maternal abdominal tissue and the amniotic fluid only ($I_M$).

As mentioned earlier, the change in optical density can be calculated by:

$$\Delta OD = -\log_{10}\frac{I_{max}}{I_{min}} = (\varepsilon_{HbO}\Delta[HbO] + \varepsilon_{Hb}\Delta[Hb])L \cdot B \quad (21)$$

$I_{max}$ and $I_{min}$ are the intensities detected at the surface of tile maternal tissue corresponding to the maximum and minimum light intensity, respectively, caused by the arterial pulsation. This exiting intensity contains both maternal and fetal signals, i.e., $I_{max}=I_{M+F}+I_M$. If one does not know, or wishes to assume, the DC value of $I_M$, the value can be neglected, and it can be assumed that:

$$(I_M+I_{M+F})/I_{min}=I_{M+F}/I_{min} \quad (22)$$

The task is to determine the systematic error introduced by this assumption.

In this calculation it is also assumed that the light detected at different wavelengths has been exposed to equal portions of fetal modulated blood. This assumption could be true for transmission oximetry, but in this case, where back-reflected light is analyzed, two different wavelengths do not necessarily penetrate to the same depths inside the tissue. A possible solution is choosing wavelengths with penetration depths as close to each other as possible. This solution is problematic because, as the oxygen saturation in the blood changes, the wavelength dependent penetration depth also changes (Mannheimer et al., IEEE Trans. Biomed. Engineer. 44:148–156, 1997). To compensate for this one can use two different wavelength pairs for high and low oxygen saturation cases.

Figure 8A:
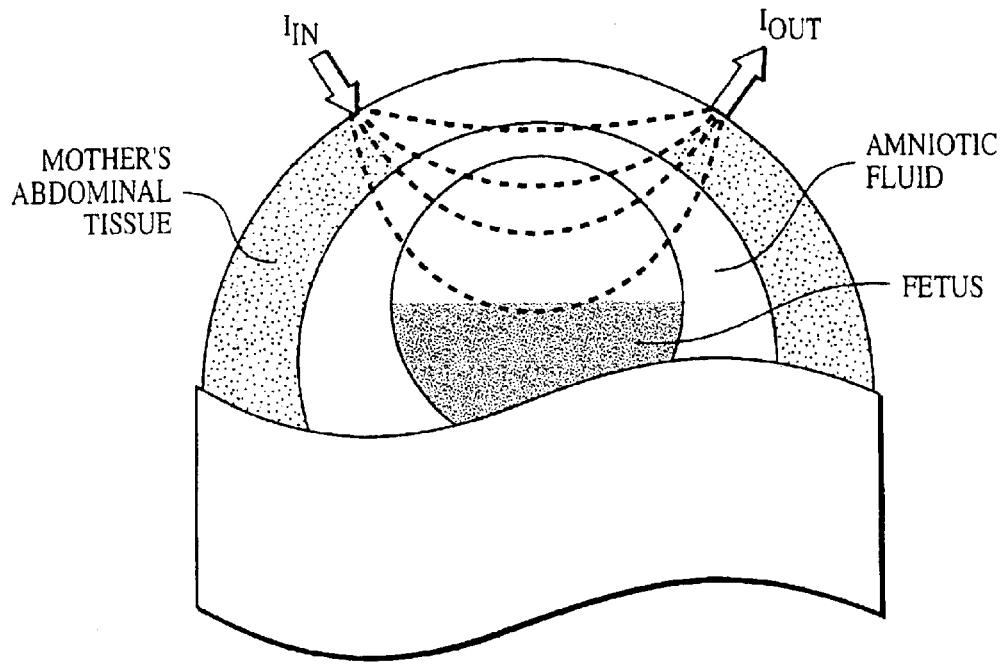
FIGS. 8A and 8B are schematic diagrams of "real" and "simulation" geometry representations, respectively.
Figure 8B:
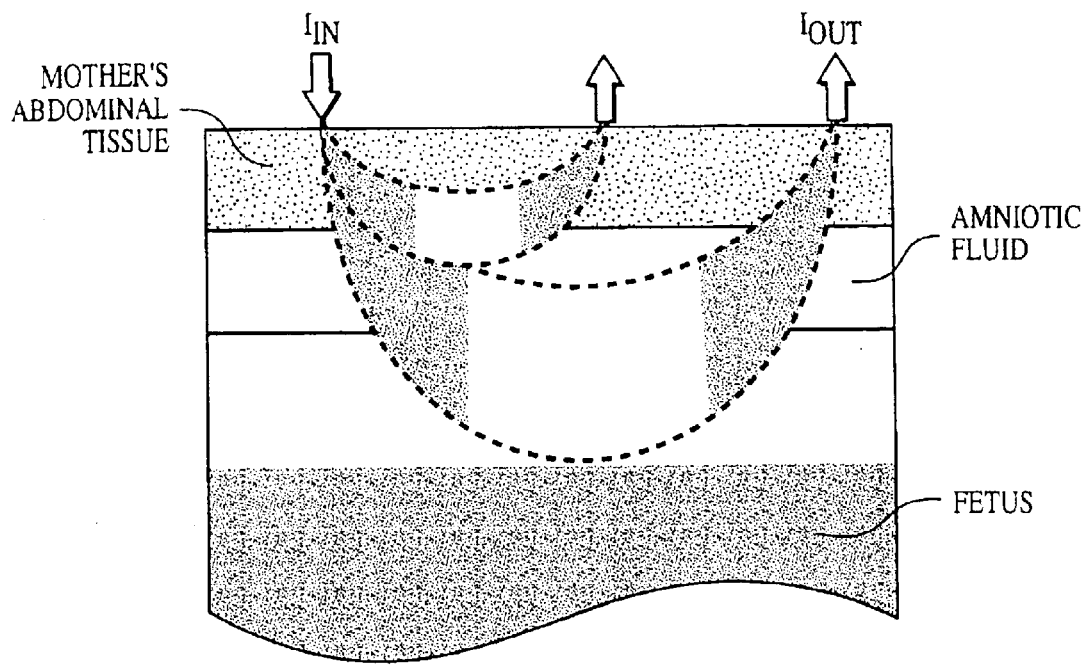

To quantify the magnitude of the optical shunt problem, a series of simulations were performed. During the simulations the maternal abdominal tissue, the fetal body, and the amniotic fluid separating the two were represented as planar layers in (x, y, z) coordinates. An example of typical simulation geometry is illustrated in FIGS. 8A and 8B.

Scattering and absorption coefficient values were assigned to each of the layers. Simulations were performed for different thicknesses of the maternal and amniotic fluid layers. The fetal layer was kept semi-infinite for all the simulations. The Monte Carlo method was used for simulating trans-abdominal measurements as described in Jacques et al. "Monte Carlo modeling of light transport in tissues," In: *Optical-Thermal Response of Laser-Irradiated Tissue*," Welch et al., eds., Plenum, New York, 1995, pp 73–100. In this method, the histories of individual photons are simulated as they undergo scattering and absorption events in the medium. Each photon is followed until it disappears (gets absorbed or has a negligible contribution) or escapes the surface of the medium and therefore gets detected. In other words, the Monte Carlo method simulates the "random walk" of the photons in the medium as perturbed by spatially varying absorption and scattering properties. The rules of photon propagation are given as probability distributions for the incremental steps of photon movement within the medium. One million photons were used in our simulation.

The simulations were made for two different cases:
(A) The maternal and amniotic layers were assigned realistic optical parameters, and the fetal layer was given an infinitely high absorption.
(B) The maternal, amniotic, and fetal layers were all given realistic optical properties.

The first simulation was performed to find the maternal signal only. The signal from the first simulation subtracted from that of the second simulation gives the fetal contribution to the total signal. The maternal layer thickness for both cases was 1 cm. The thickness of the amniotic fluid was also kept constant for both simulations and was 1 cm. The fetal layer thickness was infinite. Optical properties of the layers were chosen as follows: $\mu_{a(mother)}=0.05$ cm$^{-1}$; $\mu_{a(amniotic)}=0.012$ cm$^{-1}$; $\mu_{a(fetus)}=0.15$ cm$^{-1}$. The reduced scattering coefficient was the same for both maternal and fetal layers, and was 10 cm$^{-1}$. For the amniotic fluid, $\mu_s'=0.1$ cm$^{-1}$.

For both simulations there was a light source on the surface of the mother's abdomen, and the back-scattered light was measured for different separations from the source. The simulation also provided information on sensitivity of the detected signal to each layer of the medium. The sensitivity is a measure of how much the detected signal changes with absorption changes in each particular layer.

TABLE 1

| S/D separation (mm) | 25 | 50 | 75 |
|---|---|---|---|
| Case #1. Fetal layer with very high absorption | | | |
| Detected Signal $I_M$ | 1.51 e$^3$ | 2.89 e$^1$ | 5.12 e$^{-1}$ |
| Case #2. Optical properties of both layers are close to reality | | | |
| Detected Signal $I_{M+F} + I_M$ | 1.58 e$^3$ | 8.2 e$^1$ | 3.63 e$^1$ |
| The difference in intensities detected for the cases #1 and #2 | | | |
| $I_{M+F}$ ($I_{M+F} - I_M$) | 0.07 e$^3$ | 5.31 e$^1$ | 3.57 e$^1$ |

Table 1 indicates the detected signal at three different source/detector separations for two simulations. For the first case, the simulation corresponded to the material signal only ($I_M$), as any light reaching the fetal layer was absorbed and did not contribute to the output signal. The detected signal for the second case was the combination of both fetal and maternal signals ($I_{M+F}+I_M$). By subtracting the result of the first simulation from the second simulation, the amount of light that sampled the fetal layer, which we denote as $I_{M+F}$, was obtained.

TABLE 2

| S/D separation (mm) | 25 | 50 | 75 |
|---|---|---|---|
| Total Detected Signal | 1.58 e3 | 8.2 e1 | 3.63 e1 |
| Fraction of light in the "Maternal" layer $I_M^{frac}$ | 0.95 | 0.35 | 0.014 |
| Fraction of light in the Fetal layer $I_F^{frac}$ | 0.05 | 0.65 | 0.986 |

Table 2 shows the fraction of the total detected signal (for three different source/detector separations) that reaches each layer. The fraction of light in the maternal layer represents the shunt signal. We see that the shunt signal dominates at the 25 mm source/detector separation. At the 50 mm separation, 35% of the total detected signal passes through the maternal and amniotic layers without reaching the fetal layer, and 65% of it reaches the fetus. At the separation of 75 mm the shunting signal is only 1.4%.

How does the shunt affect the accuracy of the fetal oxygen saturation measurement? As seen above, in order to obtain oxygen saturation one needs to measure the change in optical density due to arterial pulsations. The change in optical density is given as the log of the ratio of the transmitted intensity amplitudes of the pulsatile ("ac") component to the non-pulsatile ("dc") component. Suppose there is 5% modulation in the absorption coefficient of the fetal layer (i.e., $\Delta\mu_{a(fetal)}/\mu_{a(fetal)}=5\%$), caused by fetal arterial pulsations. Then the fraction of the fluctuations of the total output signal caused by the arterial pulsations of the fetal layer only, can be calculated as:

$$\left(\frac{\partial I_{total}}{\partial \mu_{a,fetal}}\right)\frac{1}{I_{total}}\Delta\mu_{fetal} = \frac{\partial I_{M+F}}{\partial \mu_{a,fetal}} \cdot \frac{\Delta\mu_{a,fetal}}{I_{total}} = \frac{\Delta I_{M+F}}{I_{total}} \quad (23)$$

where $I_{total}$ is the total signal detected at the surface of the medium, and $\Delta I_{M+F}$ is the fraction of the total output signal modulation caused by absorption modulations in the fetal layer. The change in optical density that was actually measure is given as:

$$\Delta OD_{meas} = -\log_{10}\frac{I_{total} + \Delta I_{M+F}}{I_{total}} = -\log_{10}\left(1 + \frac{\Delta I_{M+F}}{I_{total}}\right) \approx \frac{\Delta I_{M+F}}{I_{total}} \quad (24)$$

What should be measured is the change in optical density corrected to remove the shunt signal:

$$\Delta OD_{real} = -\log_{10}\frac{I_{M+F} + \Delta I_{M+F}}{I_{M+F}} = -\log_{10}\left(1 + \frac{\Delta I_{M+F}}{I_{M+F}}\right) \approx \frac{\Delta I_{M+F}}{I_{M+F}} \quad (25)$$

The fractional error between the measured and real values of the optical densities is:

$$\text{Fractional Error} = \frac{\Delta OD_{meas} - \Delta OD_{real}}{\Delta OD_{real}} = \frac{I_{M+F}}{I_{total}} - 1 \quad (26)$$

To obtain oxygen saturation, a measurement at two different wavelengths is desirable. The data simulated at two wavelengths with various optode separations are shown in Table 3 below.

TABLE 3

| Optode Separation | Fractional Error in OD (eqn. 26) @ 700 nm | @ 900 nm | Fractional Error in Saturation |
|---|---|---|---|
| 25 mm | 26% | 36% | 5.00% |
| 50 mm | 4% | 4% | 0.46% |
| 75 mm | 3% | 4% | 1.40% |
| 100 mm | 3% | 4% | 1.00% |

In Table 3, the fractional errors resulting from measurements made at 700 and 900 nm with a fetal and maternal oxygen saturation of 85% is shown. The total hemoglobin concentration for the fetus and mother's abdominal tissue was assumed to be 0.1 mM and 0.025 mM, respectively. The reduced scattering coefficient was held constant at 10 cm$^{-1}$.

From Table 3, one see that the fractional errors between the measured value of the optical density and the desired OD can be quite large (>20%), but they are nearly the same at the two different wavelengths. For the saturation calculation, relative measurements at two different wavelengths are used. The third data column in Table 3 shows the fractional error between the saturation values calculated using, measured and desired values of the optical densities. These results indicate that, when the systematic errors at the two wavelengths caused by the optical shunt are nearly the same, the ratio tends to reduce (or cancel) the error, resulting in a relatively more accurate value for the oxygen saturation.

In conclusion, though at one wavelength the error in the OD due to the optical shunt can be significant (especially at the smaller separations, where the shunt is larger), a relative measurement at two different wavelengths significantly reduces the systematic error to a more acceptable level. This result is valid for a wide range of values for the optical parameters and structure of the maternal and fetal layers.

Therefore, one method for correcting this error is to provide a model medium formed of at least two layers of known materials with known physical and optical characteristics. By monitoring the signals obtained by emitting light into this material, and changing the characteristics of the material (e.g., the thickness of one layer), one can estimate the magnitude and contribution of the wavelength error. Once the particular contributions are obtained, these parameters can be used to normalize signals from a patient.

Example 2

A Clinical Study

The goal of this pilot clinical study was to indicate feasibility for non-invasively obtaining fetal arterial oxygen saturation values through the mother's abdomen. The subject population included women selected for the Non Stress Test (NST), which measures fetal heart rate accelerations associated with spontaneous fetal movements in utero. Initially, all women undergoing NST were eligible for this test. This study was reviewed and approved by the Institutional Review Boards of the University of Pennsylvania and written consent was obtained from all patients who participated. In addition to the ultrasound transducer and tocodynamometer employed in the NST test, the optical sensors were attached on either side of the patient's abdomen, with a light source on one side of the abdomen and the detector on the other side of the abdomen to afford light transmission through the uterus and fetus. Measurements were obtained at a single wavelength to demonstrate that the fetal pulse modulation of the optical signal can be discriminated from the maternal signal.

The Optical Fetal Monitor unit (FIG. 9) contained at least five modules; the system power supply; the laser source; the control module; the optode assembly, and the computer. The laser source generates the optical signal, which reaches the optode assembly through a 1 mm diameter silica fiber. Its output is modulated at a fixed frequency of 2 kHz to permit synchronous detection.

The system consisted of a single wavelength light source and four separate optical detectors. The detectors, each spaced one inch (2.5 cm) apart on the optode assembly (FIG. 10), were coupled to the patient through a short, 3 mm-thick plastic light guide. This 3 mm light pipe was used to both improve electrical isolation and to couple as much light as possible from the mother's abdomen to the silicon detectors. The photo-detector's electrical outputs travel back through the umbilical cable to the control module, where the output from each detector is appropriately processed.

Synchronous detection was used to both reduce extraneous interference from ambient light sources and to improve the signal to noise ratio of the measurements by reducing the contribution of 1/f noise. The modulated optical signal was processed by first passing the detector output through a high pass filter, and then through a demodulator. The demodulator shifted the 2 kHz signal to a DC level. All other stray light signals exited the detector as frequency-shifted AC signals. The signal-to-noise ratio on the DC level was then improved by reducing the bandwidth with a low-pass filter. However, the bandwidth had to be large enough not to suppress the fetal signal. The bandwidth of our filter was 16 Hz. The four amplified and filtered DC outputs then pass from the control module to the computer for digital acquisition. The signals were digitized at a constant rate and stored in memory. The fetal heart rate was simultaneously monitored with a maternal trans-abdominal Doppler probe from a cardiotocograph recorder. Fetal depth was determined by ultrasound just before and after the optical measurements.

Figures 11A, 11B:
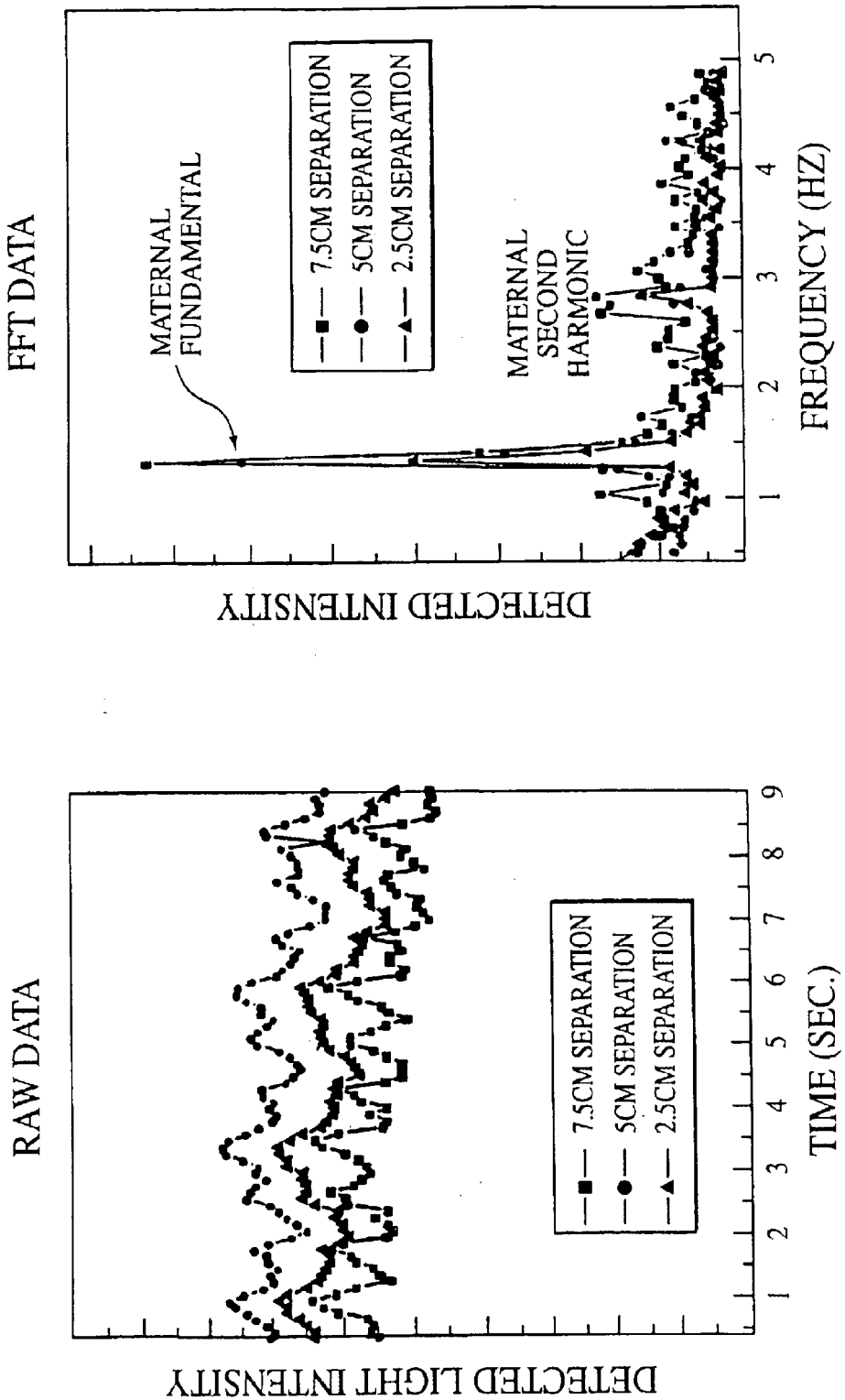
FIGS. 11A, 11B, 12A, and 12B are graphs of frequency versus light intensity.

Experiments were performed on 17 patients. The preliminary results indicated feasibility for trans-abdominal fetal pulse oximetry. FIGS. 11A and 11B summarize the collected data before and after the Fourier transform was performed. The optical signals were slightly modulated by the heart as the elastic vessels expanded and then relaxed with each ventricular contraction. The momentary increase in blood volume increased the light absorption. The detected light signal thus exhibited a signal amplitude modulation in the general shape of a saw-tooth (FIG. 11A); a sharp drop in signal corresponding to the ventricular contraction, followed by a slower return as the blood emptied through the capillaries on its way back to the heart. The peaks on the Fourier transformed data (FIG. 11B) represent the fundamental and first harmonics of the mother's heart.

Figure 12B:
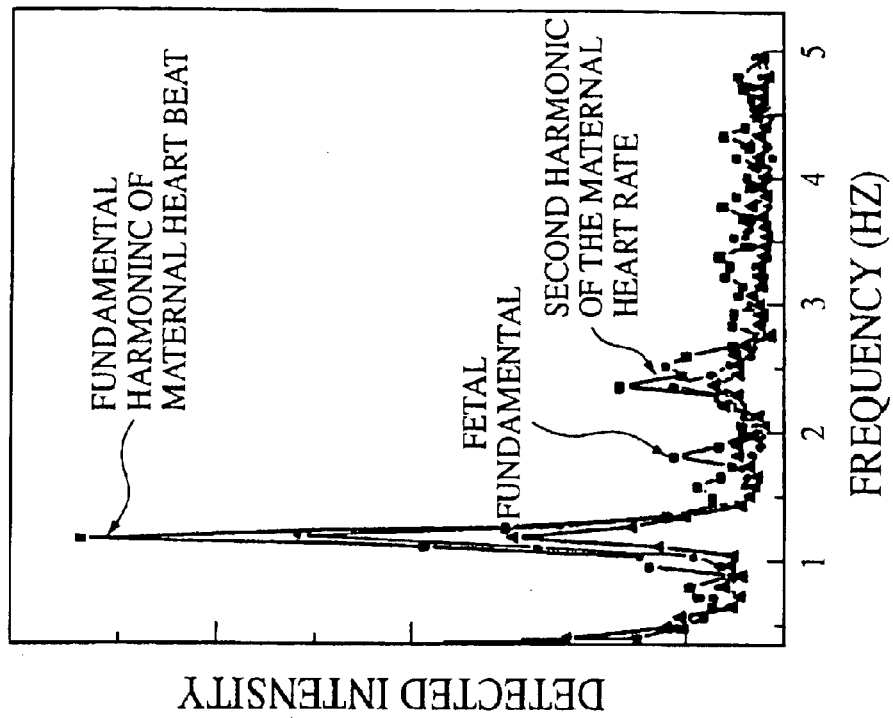
Figure 12A:
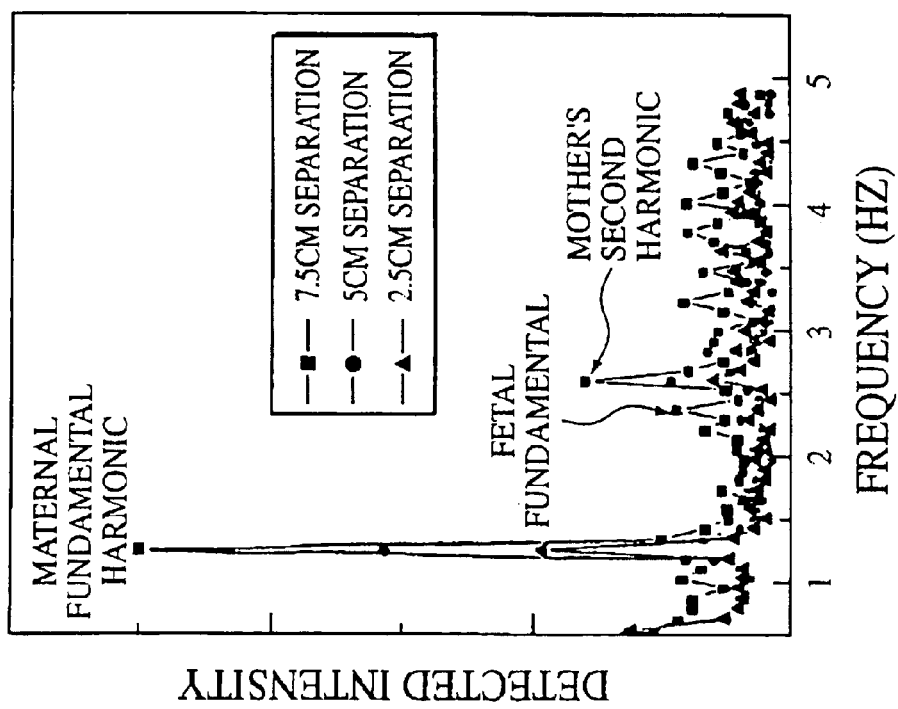

Since the fetal pulse is generally faster than the maternal pulse, the respective contributions to the optical signals should appear as separate peaks in the Fourier transform. FIGS. 12A and 12B demonstrate that it was possible to observe the fetal heart rate and discriminate it from the mother's. The depth of the fetal head from the surface of the mother's abdomen for this particular case was 2.2 cm. In particular, the fetal heart rate lies between the fundamental and second harmonic of the maternal heart rate. The fetal heart rate was simultaneously monitored by cardiotocography and echography.

A correlation between the detected signal and the depth of the fetus from the surface of the mother's abdomen (as determined by ultrasound) was confirmed. When the fetal depth was more then 3.5 cm, the detected fetal signal was weak and difficult to interpret. The signal improved as the depth decreased.

Figure 13:
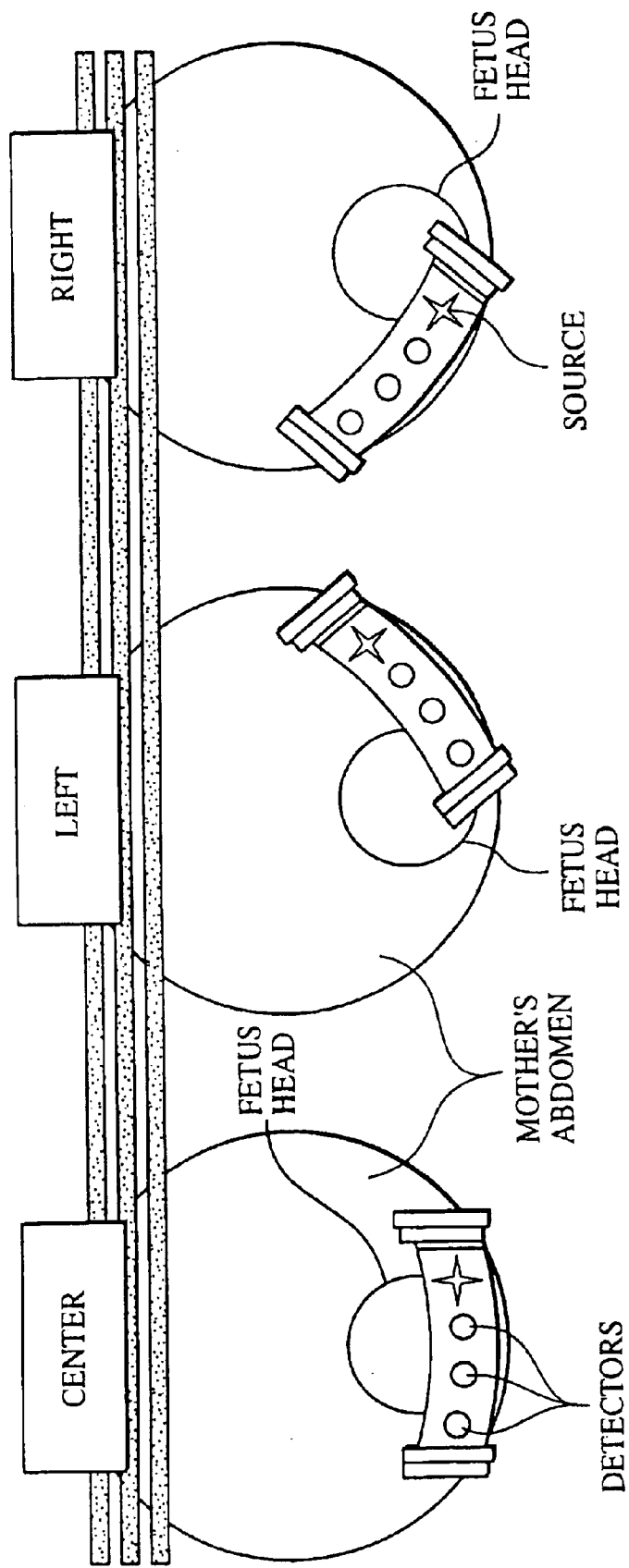
FIG. 13 is a schematic diagram of three different probe positions suitable for use in the methods and devices of the invention.

All measurements were performed for three different probe positions, as illustrated in FIG. 13, to investigate the dependence of probe position relative to fetal position. For the case when the probe was placed on the left side of the mother's abdomen with the source far to the left of the fetal head, it was not possible to detect the fetal signal using this particular experimental design. For the two other cases, central and right probe positions, the fetal signal was easily detected. The summary of the results is presented in Tables 4–7.

TABLE 4

Signal-to-noise ratio dependence on the probe and fetus position.
Total Number of Subjects (Patients) = 17

| | | Signal Strength (best case per patient) | | |
|---|---|---|---|---|
| | | S/N ≥ 2 ("Good" results) | S/N < 2 ("not bad" res.) | S/N = 0 (no signal) |
| Overall | | 5 patients | 6 patients | 6 patients |
| Depth of the fetal head from mother's skin | <1.8 cm | 20% (1) | 33% (2) | 17% (1) |
| | 1.8–3 cm | 60% (3) | 50% (3) | 33% (2) |
| | >3 cm | 20% (1) | 17% (1) | 50% (3) |

Table 4 shows that, when the depth of the fetal head was greater than 3 cm, the signal to noise ration (SNR) was less than 2 in 50% of the patients. This occurs because the detected light is unable to penetrate these depths. The best results were obtained at depths between 1.8 and 2.5 cm, which occurred in 60% of the patients, indicating an SNR greater than 2. As one can see from Table 4, there was a decrease in the signal to SNR for depths below 1.8 cm.

In certain circumstances, one may be able to achieve a 1.8 to 2.5 cm distance between the optode and the fetus by simply pressing the emitter optode into the abdomen. For example, if the fetus happens to be 3 cm from the abdominal skin surface, a device can apply the necessary pressure on the emitter optode against the abdomen to displace or compress maternal tissue, thereby placing the emitter optode within 2.5 cm of the fetus.

TABLE 5

Signal dependence on frequency difference in fetal fundamental and maternal second harmonics.
Total Number of Subjects (Patients) = 17

| | | Signal Strength (best case per patient) | | |
|---|---|---|---|---|
| | | S/N ≥ 2 ("Good" results) | S/N < 2 ("not bad" res.) | S/N = 0 (no signal) |
| Overall | | 5 patients | 6 patients | 6 patients |
| Difference in maternal and fetal heart rates | Δf > .1 Hz | 60% (3) | 66.6% (4) | 16.6% (1) |
| | 005 < Δf < .1 Hz | 20% (1) | 16.6% (1) | 16.6% (1) |
| | Δf < .005 | 20% (1) | 16.6% (1) | 66.6% (4) |

Table 5 summarizes the dependence of measurements on the frequency difference in fetal fundamental and maternal second harmonics. The peaks are easy to discriminate when the frequency difference is greater then 0.1 Hz. The peaks are more difficult to resolve for smaller frequency difference because of peak overlap.

TABLE 6

Signal correlation with position of the probe on the mother's abdomen

| Probe position | S/N ≥ 2 ("Good" results) | S/N < 2 ("not bad" res.) | S/N = 0 (no signal) |
|---|---|---|---|
| Left (# patients - 17) | 12% (2 patients) | 12% (2) | 76% (13) |
| Center (# patients - 17) | 59% (10) | 29% (5) | 12% (2) |
| Right (# patients - 17) | 70% (12) | 18% (3) | 12% (2) |

The localization experiments revealed (Table 6) that the best positioning of the probe on the mother's abdomen was on the right side or center (FIG. 13). The left position of the probe generally did not produce a signal above the noise floor. This is most likely a result of the large distance between the source and fetus, and thus the fetal pulse contributed weakly to the optical signal. For the center and right probe position, however, the light source was near the fetal head and thus the fetal pulse had a stronger contribution to the optical signal. In other words, when the source was close to the fetal head, a large fraction of the detected signal had actually sampled the fetus.

TABLE 7

Signal dependence on the source/detector separation.

| S/D separation | Fetal Depth: | | |
|---|---|---|---|
| | <1.8 cm | 1.8–3 cm | >3 cm |
| 2.5 cm | S/N < 2 | S/N ≧ 2 | S/N << 2 |
| 5.0 cm | S/N < 2 | S/N ≧ 2 | S/N < 2 |
| 7.5 cm | S/N << 2 | S/N < 2 | S/N < 2 |
| 10 cm | S/N = 0 | S/N = 0 | S/N = 0 |

The dependence of the detected light intensity on the source/detector separation for three different depth ranges is given in Table 7. As one can see, the best results were obtained for fetal depth of 1.8 to 3 cm at all three source/detector separations. The signal strength decreased with the fetal depth less then 1.8 cm or more than 3 cm. The signal was too weak at a 10 cm source-detector separation.

These results demonstrated the possibility of obtaining fetal signal through the mother's abdomen. It has been demonstrated herein that trans-abdominal fetal pulse oximetry is feasible.

Example 3

Pulse Oximetry Using Two Wavelengths

Figure 9:
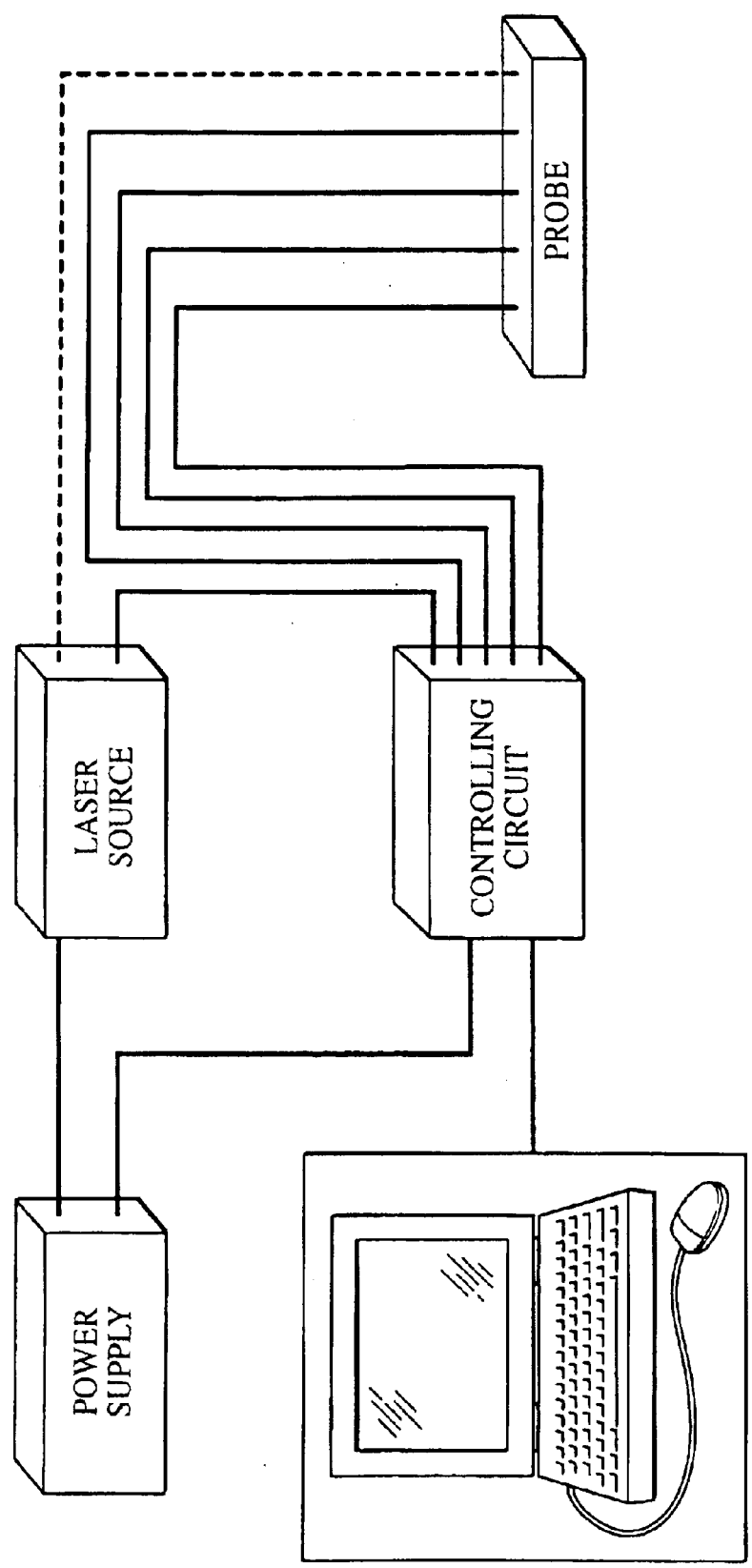
FIG. 9 is a schematic diagram of an optical fetal monitor block diagram. Solid lines represent detector fibers, and dotted lines represent source fibers.
Figure 10:
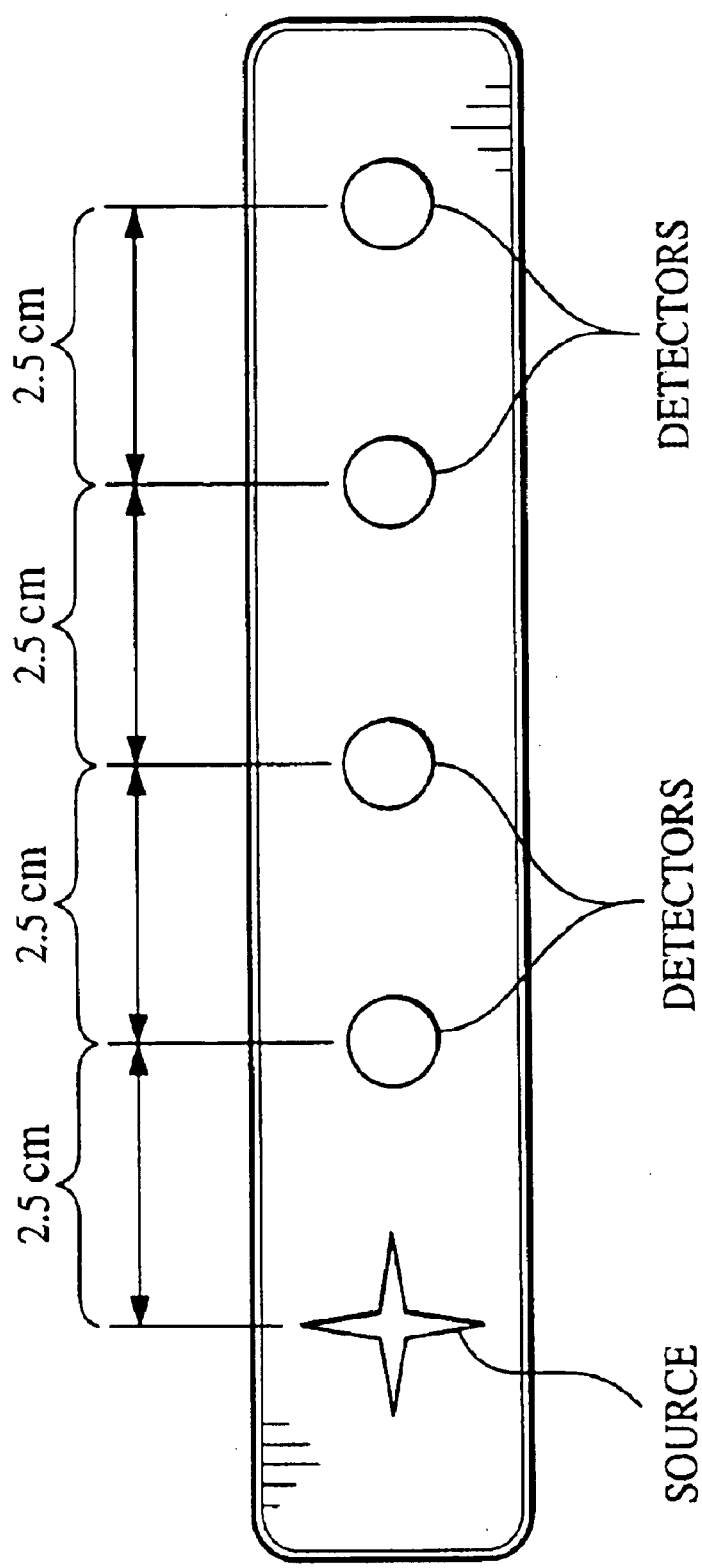
FIG. 10 is a schematic diagram of an optical probe configuration.

Fetal arterial blood saturation is measured using the procedures and devices described in Example 2 above, with the following modifications (FIGS. 9 and 10). The emitter optode delivers light of two specific wavelengths, 700 nm and 830 nm. Both wavelengths of light are emitted and detected simultaneously. The intensity of back-scattered light of both wavelengths is detected at the abdominal surface and converted into electronic signals. A Fourier transform of the signals removes the maternal contribution so that the fetal contributions can be isolated. The fetal oxygen saturation (S) is then calculated using equations (7) and (8), which are described above.

Other Embodiments

It is to be understood that while the invention has been described in conjunction with the detailed description thereof, the foregoing description is intended to illustrate and not limit the scope of the invention, which is defined by the scope of the claims. Other aspects, advantages, and modifications are within the scope of the following claims.

What is claimed is:

1. A method of determining the oxygen saturation of fetal blood, the method comprising emitting light of a first wavelength onto the abdominal surface of a pregnant mammal over time;

emitting light of a second wavelength onto the abdominal surface of the pregnant mammal over time, wherein the second wavelength is different from the first wavelength;

detecting the intensity of light scattered by fetal and maternal arterial blood at the first wavelength and light scattered by fetal and maternal arterial blood at the second wavelength over time, wherein the time of detection is sufficient to record at least one fetal heart beat and at least one maternal heart beat;

converting the detected light into electronic signals;

processing the electronic signals to separate maternal and fetal contributions to the electronic signals;

removing the contributions to the electronic signals generated by maternal arterial blood;

measuring the absorption of light at the first and second wavelengths by fetal arterial blood; and calculating the oxygen saturation of the fetal arterial blood from the measured absorption of light over time.

2. The method of claim 1, wherein the first wavelength is about 655–705 nm.

3. The method of claim 1, wherein the first wavelength is about 700 nm.

4. The method of claim 1, wherein the second wavelength is about 820–910 nm.

5. The method of claim 1, wherein the second wavelength is about 830 nm.

6. The method of claim 1, wherein the electronic signals are processed using a Fourier transform.

7. The method of claim 1, further comprising emitting light of a third wavelength, wherein the third wavelength is different from each of the first and second wavelengths;

detecting the intensity of light scattered by fetal and maternal arterial blood at the third wavelength; and measuring the absorption of light at the third wavelength.

8. The method of claim 7, further comprising emitting light of a fourth wavelength, wherein the fourth wavelength is different from each of the first, second, and third wavelengths;

detecting the intensity of light scattered by fetal and maternal arterial blood at the fourth wavelength; and measuring the absorption of light at the fourth wavelength.

9. The method of claim 1, further comprising removing the contributions to the signals generated by light that never passes through fetal tissue.

10. A fetal pulse oximeter comprising a first light source emitting light at a first wavelength;

a second light source emitting light at a second wavelength, wherein the second wavelength is different from the first wavelength;

one or more photodetectors suitable for detecting light at the first wavelength and light at the second wavelength, the photodetector capable of distinguishing light at the first wavelength from light at the second wavelength;

a probe configured to engage an abdominal surface of a pregnant mammal, the probe coupling the first and second light sources to the photodetector at a substantially fixed position when the probe is engaged to the abdominal surface; and a processor configured to (1) process the electronic signals generated by the photodetectors in response to detection of light at the first and second wavelengths, (2) remove the contributions to the signals generated by maternal arterial blood, (3) determine the absorption of light at the first and second wavelengths by fetal arterial blood, and (4) calculate the oxygen saturation of the fetal arterial blood from the absorbed light over time.

11. The oximeter of claim 10, wherein the first wavelength is about 655–705 nm.

12. The oximeter of claim 10, wherein the first wavelength is about 700 nm.

13. The oximeter of claim 10, wherein the second wavelength is about 820–910 nm.

14. The oximeter of claim 10, wherein the second wavelength is about 830 nm.

15. The oximeter of claim 10, wherein the processor processes the electronic signals using a Fourier transform.

16. The oximeter of claim 10, further comprising
a third light source emitting light of a third wavelength, wherein the third wavelength is different from each of the first and second wavelengths; and
one or more photodetectors suitable for detecting light at the third wavelength.

17. The oximeter of claim 16, further comprising
a fourth light source emitting light of a fourth wavelength, wherein the fourth wavelength is different from each of the first, second, and third wavelengths; and
one or more photodetectors suitable for detecting light at the fourth wavelength.

18. The oximeter of claim 10, wherein the processor is further configured to remove the contributions to the signals generated by light that never passes through fetal tissue.

* * * * *

UNITED STATES PATENT AND TRADEMARK OFFICE
CERTIFICATE OF CORRECTION

PATENT NO. : 7,047,055 B2  
APPLICATION NO. : 10/415163  
DATED : May 16, 2006  
INVENTOR(S) : David Alan Boas and Anna Zourabian Page 1 of 1

It is certified that error appears in the above-identified patent and that said Letters Patent is hereby corrected as shown below:

Title page item (73), Assignees' name: should read --

(73)    Assignee:    The General Hospital Corporation, Boston, MA (US);  
    Tufts University, Boston, MD (US)

Signed and Sealed this

Eighteenth Day of July, 2006

JON W. DUDAS  
*Director of the United States Patent and Trademark Office*

UNITED STATES PATENT AND TRADEMARK OFFICE
CERTIFICATE OF CORRECTION

PATENT NO. : 7,047,055 B2  Page 1 of 1
APPLICATION NO. : 10/415163
DATED : May 16, 2006
INVENTOR(S) : David Alan Boas and Anna Zourabian It is certified that error appears in the above-identified patent and that said Letters Patent is hereby corrected as shown below:

Following INID code (73), please fix Assignees' name:

(73) Assignees: The General Hospital Corporation, Boston, MA (US);
Tufts University, Boston, MA (US)

Signed and Sealed this

Fifth Day of September, 2006

JON W. DUDAS
*Director of the United States Patent and Trademark Office*

UNITED STATES PATENT AND TRADEMARK OFFICE
CERTIFICATE OF CORRECTION

PATENT NO. : 7,047,055 B2  
APPLICATION NO. : 10/415163  
DATED : May 16, 2006  
INVENTOR(S) : David Alan Boas and Anna Zourabian Page 1 of 1

It is certified that error appears in the above-identified patent and that said Letters Patent is hereby corrected as shown below:

Title page item (73), Assignees' name: should read

-- (73)    Assignee:    The General Hospital Corporation, Boston, MA (US);  
    Tufts University, Boston, MA (US) --

This certificate supersedes Certificate of Correction issued July 18, 2006.

Signed and Sealed this

Nineteenth Day of September, 2006

JON W. DUDAS  
*Director of the United States Patent and Trademark Office*